United States Patent
Limketkai et al.

(10) Patent No.: US 9,816,049 B2
(45) Date of Patent: Nov. 14, 2017

(54) FRAGRANCE-CONTAINING CYCLODEXTRIN-BASED METAL ORGANIC FRAMEWORKS

(71) Applicant: PanaceaNano, Inc., Aliso Viejo, CA (US)

(72) Inventors: Benjie N. Limketkai, Hesperia, CA (US); Youssry Y. Botros, Aliso Viejo, CA (US)

(73) Assignee: PanaceaNano, Inc., Aliso Viejo, CA (US)

( * ) Notice: Subject to any disclaimer, the term of this patent is extended or adjusted under 35 U.S.C. 154(b) by 0 days.

(21) Appl. No.: 15/352,809

(22) Filed: Nov. 16, 2016

(65) Prior Publication Data

US 2017/0137744 A1 May 18, 2017

Related U.S. Application Data

(60) Provisional application No. 62/256,423, filed on Nov. 17, 2015.

(51) Int. Cl.
*A61K 8/00* (2006.01)
*C11B 9/00* (2006.01)

(52) U.S. Cl.
CPC ............ *C11B 9/008* (2013.01); *C11B 9/0003* (2013.01); *C11B 9/0007* (2013.01); *C11B 9/0015* (2013.01); *C11B 9/0019* (2013.01)

(58) Field of Classification Search
CPC ..... C11B 9/008; C11B 9/0015; C11B 9/0007; C11B 9/0003; C11B 9/0019
USPC ........................................................ 512/2, 1
See application file for complete search history.

(56) References Cited

U.S. PATENT DOCUMENTS

| | | | |
|---|---|---|---|
| 2,886,446 A | 5/1959 | Kramer | |
| 3,258,400 A | 6/1966 | Houlihan | |
| 3,920,849 A | 11/1975 | Marmo et al. | |
| 3,939,099 A | 2/1976 | Tusa et al. | |
| 4,252,986 A | 2/1981 | Klein et al. | |
| 4,303,787 A | 12/1981 | Horikoshi et al. | |
| 4,384,898 A | 5/1983 | Okada et al. | |
| 4,568,560 A | 2/1986 | Schobel | |
| 4,808,232 A | 2/1989 | Beesley | |
| 4,835,105 A | 5/1989 | Seres et al. | |
| 4,849,400 A | 7/1989 | King | |
| 5,051,305 A | 9/1991 | Whitaker, Sr. | |
| 5,238,915 A * | 8/1993 | Fuwa | A61K 8/738 512/4 |
| 6,110,449 A * | 8/2000 | Bacon | A61K 8/738 422/5 |
| 6,172,037 B1 | 1/2001 | Paring et al. | |
| 6,177,413 B1 | 1/2001 | Blahut | |
| 6,458,754 B1 | 10/2002 | Velazquez et al. | |
| 6,558,706 B2 | 5/2003 | Kantor et al. | |
| 8,709,072 B2 | 4/2014 | Rahi et al. | |
| 8,871,473 B2 | 10/2014 | Wu | |
| 9,085,460 B2 | 7/2015 | Stoddart et al. | |
| 9,399,803 B2 | 7/2016 | Stoddart et al. | |
| 2003/0092600 A1 | 5/2003 | Shepherd, Jr. | |
| 2005/0255069 A1 * | 11/2005 | Muller | A61Q 19/10 424/70.13 |
| 2008/0054089 A1 | 3/2008 | Oldfield et al. | |
| 2008/0206823 A1 | 8/2008 | Jacobson et al. | |
| 2011/0052650 A1 | 3/2011 | Morris et al. | |
| 2012/0070904 A1 * | 3/2012 | Stoddart | B01J 20/226 436/133 |
| 2013/0171228 A1 | 7/2013 | Morris | |
| 2013/0313193 A1 | 11/2013 | Nair et al. | |
| 2014/0105842 A1 | 4/2014 | Pan et al. | |
| 2014/0220112 A1 | 8/2014 | Szoka, Jr. et al. | |
| 2014/0311297 A1 | 10/2014 | Stoddart et al. | |
| 2015/0150981 A1 | 6/2015 | Gref et al. | |
| 2015/0322174 A1 | 11/2015 | Stoddart et al. | |
| 2017/0203073 A1 | 7/2017 | Dor-Zidon | |

FOREIGN PATENT DOCUMENTS

| | | |
|---|---|---|
| CN | 104888235 A | 9/2015 |
| JP | H05-076756 A | 3/1993 |
| WO | 2007035596 A2 | 3/2007 |
| WO | 2016010522 A1 | 1/2016 |

OTHER PUBLICATIONS

Wind, et al.; "Engineering of factors determining a-amylase and cyclodextrin glycosyltransferase specificity in the cyclodextrin glycosyltransferase from Thermoanaerobacterium thermosulfurigenes EM1"; Jan. 6/Feb. 23, 1998; pp. 598-605.
McKinlay, et al.; "BioMOFs: Metal-Organic Frameworks for Biological and Medical Applications"; 2010; pp. 6260-6266.
Smaldone, et al.; "Metal-Organic Frameworks from Edible Natural Products"; 2010; pp. 8630-8634.
Gassensmith, et al.; "Strong and Reversible Binding of Carbon Dioxide in a Green Metal—Organic Framework"; 2011; pp. 15312-15315.
Forgan, et al.; "Nanoporous Carbohydrate Metal—Organic Frameworks"; 2012; pp. 406-417.
Gassensmith, et al.; "A Metal—Organic Framework-Based Material for Electrochemical Sensing of Carbon Dioxide"; 2014; pp. 8277-8282.
Gassensmith, et al.; "A Metal—Organic Framework-Based Material for Electrochemical Sensing of Carbon Dioxide"; Supplementary Information; 2014; pp. S1-S12.
Liu, et al.; "Second-Sphere Coordination Revisited"; 2014; pp. 315-320.
Liu, et al.; "Extended metal-carbohydrated frameworks"; 2014; pp. 1-14.

* cited by examiner

*Primary Examiner* — Jessica Whiteley

(57) ABSTRACT

This disclosure relates to a composition containing a fragrance and a porous cyclodextrin-based metal organic framework (CD-MOF). The CD-MOF includes at least a metal cation and a plurality of cyclodextrin molecules.

26 Claims, 28 Drawing Sheets

US 9,816,049 B2

FRAGRANCE-CONTAINING CYCLODEXTRIN-BASED METAL ORGANIC FRAMEWORKS

CROSS REFERENCE TO RELATED APPLICATION

Pursuant to 35 U.S.C. §119(e), this application claims priority to U.S. Provisional Application Ser. No. 62/256,423, filed Nov. 17, 2015, the contents of which are hereby incorporated by reference.

TECHNICAL FIELD

This disclosure relates to compositions containing at least one fragrance and at least one cyclodextrin-based metal organic framework (CD-MOF), as well as related components, products, and methods.

BACKGROUND

Cyclodextrins (cyclic dextrins, cyclic oligosaccharides, CDs) are cyclic structures composed of D-glucopyranosyl residues linked in a ring by α-1,4 glycosidic bonds. Glucose molecules, bonded together in the ring, form a hollow, circular, truncated cone with a hydrophobic interior and a hydrophilic exterior. This structure gives CDs the ability to host guest molecules (complexant) within their cavity. Due to this ability to form inclusion compounds (complex) with a wide variety of chemicals, thereby acting as a carrier to encapsulate, stabilize, and/or alter the chemical and physical properties, e.g., volatility and solubility, of the guest molecules, CDs have been widely used in the agricultural, food, pharmaceutical, and chemical industries. The common αCD, βCD, and γCD consist of six, seven, and eight glucopyranose units in their ring, respectively.

SUMMARY

This disclosure is based on the unexpected discovery that adding a CD-MOF into a composition containing a fragrance molecule can significantly improve the scent profile of the fragrance composition (e.g., by increasing the average fragrance strength, the effective duration, and/or the fragrance fill factor of the fragrance composition).

In one aspect, this disclosure features a composition containing a fragrance and a porous cyclodextrin-based metal organic framework (CD-MOF). The CD-MOF includes at least a metal cation and a plurality of cyclodextrin molecules. The composition includes from about 0.01 μL to about 10 μL of the fragrance per 1 mg of the CD-MOF.

In another aspect, this disclosure features a composition containing a first component that includes a first porous CD-MOF and a first fragrance; and a second component that includes a second CD-MOF and a second fragrance. The first CD-MOF includes at least a first metal cation and a plurality of first cyclodextrin molecules. The second CD-MOF includes at least a second metal cation and a plurality of second cyclodextrin molecules. The first component is prepared by mixing the first CD-MOF and the first fragrance at a first ratio, the second component is prepared by mixing the second CD-MOF and the second fragrance at a second ratio, and the first ratio is different from the second ratio.

In still another aspect, this disclosure features a composition that includes a fragrance and a porous CD-MOF, in which the CD-MOF has an average particle size of from about 10 nm to about 1 cm and includes at least a metal cation and a plurality of cyclodextrin molecules. The composition is a suspension, an emulsion, or a gel.

Embodiments can include one or more of the following features.

In some embodiments, the composition includes from about 0.1 μL to about 5 μL (e.g., from about 0.5 μL to about 2 μL) of the fragrance per 1 mg of the CD-MOF.

In some embodiments, the CD-MOF has an average particle size of from about 10 nm to about 1 μm or from about 1 μm to about 1 cm.

In some embodiments, the composition further includes a carrier. The carrier can include a solvent, an oil, or a combination thereof.

In some embodiments, the composition further includes a fixative. The fixative can include an ester, an alcohol, a ketone, a resin, or a musk.

In some embodiments, the first fragrance is different from the second fragrance.

In some embodiments, the first component includes from about 0.5 μL to about 2 μL of the first fragrance per 1 mg of the first CD-MOF.

In some embodiments, the second component includes from about 0.1 μL to about 0.5 μL of the second fragrance per 1 mg of the second CD-MOF.

In some embodiments, the first CD-MOF has a first average particle size, the second CD-MOF has a second average particle size, and the first average particle size is different from the second particle size. For example, the first average particle size can be from about 10 nm to about 1 μm and the second average particle size can be from about 1 μm to about 1 cm.

Other features, objects, and advantages of the invention will be apparent from the description, drawings, and claims.

DESCRIPTION OF DRAWINGS

Like reference symbols in the various drawings indicate like elements.

DETAILED DESCRIPTION

Definitions

Figure 1:
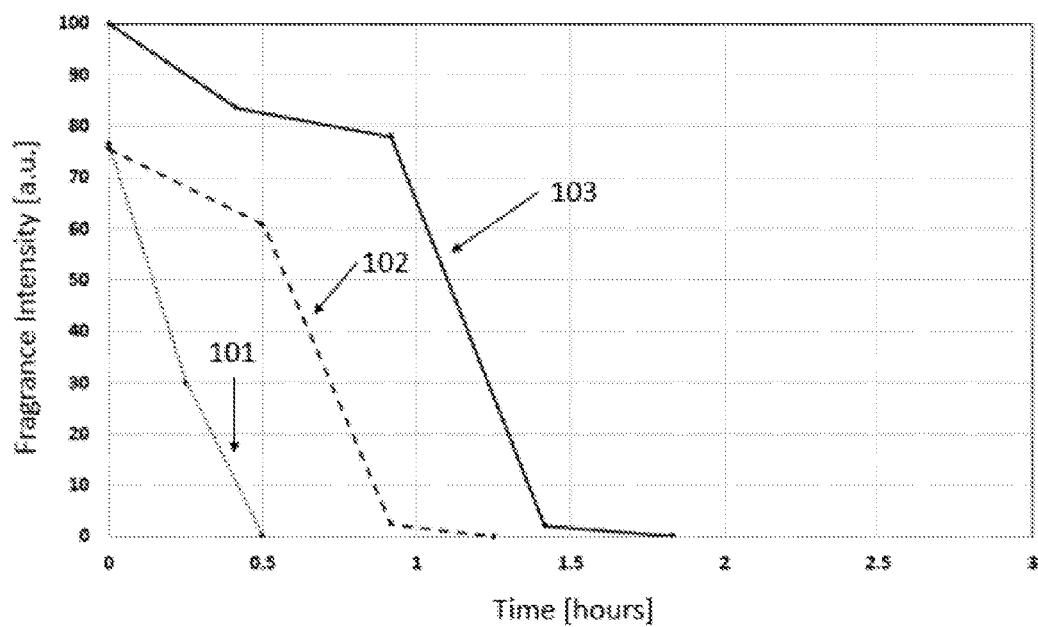
FIG. 1 is a graph showing the scent profiles of 5 μL (101), 10 μL (102), and 20 μL (103) of a lemon oil alone.

The term "fragrance" refers to a compound or a mixture of compounds that possess a scent or aroma.

The term "fixative" refers to a compound that can modify the scent profile of a fragrance composition.

The term "fragrance intensity" refers to a concentration of a fragrance in the headspace (i.e., space directly surrounding the fragrance) that would eventually reach and be sensed by the olfactory receptor system.

The term "scent profile" refers to the fragrance release plot of fragrance intensity versus time.

The term "life of fragrance" refers to the length of time for a fragrance to deplete from a fragrance composition after which any residual evaporation of the fragrance into the headspace will not exceed an odor threshold.

The term "odor threshold" refers to the minimum concentration of a fragrance that produces an appreciable perceived odor or scent.

The term "average fragrance strength" refers to the average fragrance intensity during the life of the fragrance.

The term "effective duration" refers to the length of time it takes for the fragrance intensity to drop below the average fragrance intensity.

The term "absolute duration" refers to the length of time during which the fragrance intensity is above 5% of its peak fragrance intensity.

The term "fragrance fill factor" refers to the average fragrance strength multiplied by its effective duration.

Descriptions of Fragrance Compositions

This disclosure generally relates to compositions containing at least one fragrance and at least one CD-MOF (also known as a CD-MOF complex), as well as methods of making and using of such compositions.

Exemplary fragrances include esters, aldehydes, ethers, nitriles, ketones, or alcohols. Examples of esters include methyl salicylate, ethyl propionate, allyl hexanoate, methyl 2-aminobenzoate, 2-(4-methylcyclohexyl)propan-2-yl acetate, ethyl 2-methylbutanoate, or guaiol acetate. Examples of aldehydes include cinnamaldehyde, benzaldehyde, 1-methyl-4-(4-methylpentyl)cyclohex-3-ene-1-carbaldehyde, 4-propan-2-ylbenzaldehyde, 3-(4-propan-2-ylphenyl)butanal, 1,3-benzodioxole-5-carbaldehyde, 3-(4-tert-butylphenyl)butanal, 2,4-dimethylcyclohex-3-ene-1-carbaldehyde, 1,1-dimethoxypropan-2-ylbenzene, dodec-3-enal, n-dodecanal, 3-(3-propan-2-ylphenyl)butanal, 2-benzylideneheptanal, 3-phenylprop-2-enal, 3-(1,3-benzodioxol-5-yl)-2-methylpropanal, 3-(4-methoxyphenyl)-2-methylpropanal, 2-phenylpropanal, 2-phenylacetaldehyde, 4-(4-hydroxy-4-methylpentyl)-3-cyclohexene-1-carboxaldehyde, 2-(phenylmethylidene)octanal, 4-methoxybenzaldehyde, or 2,6-dimethylhept-5-enal. An example of an ether is 2,4-dimethyl-4,4a,5,9b-tetrahydroindeno[1,2-d][1,3]dioxine. An example of a nitrile is 3,7-dimethyloct-6-enenitrile. Examples of ketones include (E)-4-(2,6,6-trimethyl-1-cyclohex-2-enyl)but-3-en-2-one, methyl cedryl ketone (also known as 1-(2,3,4,7,8,8a-hexahydro-3,6,8,8-tetramethyl-1H-ethanone), or (E)-4-(2,6,6-trimethyl-1-cyclohexenyl)but-3-en-2-one. Examples of alcohols include 3,7-dimethyl-1,7-octane diol, (Z)-3-methyl-5-(2,2,3-trimethyl-1-cyclopent-3-enyl)pent-4-en-2-ol, 2-(4-methyl-1-cyclohex-3-enyl)propan-2-ol, 3,7-dimethylocta-1,6-dien-3-ol, or hexan-1-ol. Examples of fragrances containing a mixture of compounds include the essential oils of lemon, orange, peppermint, lemongrass, rose, clove, rosemary, ylang ylang, chamomile, pine, lavender, tea tree, wintergreen, camphor, jasmine, vanilla, cedarwood, sandalwood, patchouli, and musk. In some embodiments, the fragrance can be at least about 1 wt % (e.g., at least about 5 wt %, at least about 10 wt %, at least about 15 wt %, at least about 20 wt %, at least about 25 wt %, at least about 30 wt %, at least about 40 wt %, at least about 50 wt %) and/or at most about 95 wt % (e.g., at most about 90 wt %, at most about 85 wt %, at most about 80 wt %, at most about 75 wt %, at most about 70 wt %, at most about 65 wt %, at most about 60 wt %, at most about 55 wt %, or at most about 50 wt %) of the fragrance compositions described herein.

In general, the CD-MOFs that can be used in the methods described herein can be those described in U.S. Pat. No. 9,085,460, the contents of which are hereby incorporated by reference in their entirely.

The CD-MOFs generally include at least one metal cation (e.g., a plurality of metal cations) and a plurality of cyclodextrin components (such as those of Formula (I) below). The at least one metal cation is generally coordinated with the plurality of cyclodextrin molecules or cyclodextrin derivatives. In general, the CD-MOFs are porous.

Suitable metal cations that can be used in the CD-MOFs include Group I metal cations (e.g., $Na^+$, $K^+$, $Rb^+$, or $CS^+$), Group II metal cations (e.g., $Mg^{2+}$, $Ca^{2+}$, $Sr^{2+}$, or $Ba^{2+}$), and transition metal cations (e.g., $Mn^{4+}$, $Fe^{3+}$, $Co^{2+}$, $Ni^{2+}$, $Cu^{2+}$, or $Zn^{2+}$). The metal cations can be included into the CD-MOFs by using salts or bases as starting materials. Examples of suitable salts include KF, KCl, KBr, $K_2CO_3$, $K_2$ (azobenzene-4,4'-dicarboxylate), $Na_2CO_3$, and $NaBPh_4$. Examples of suitable bases include KOH, NaOH, RbOH, and CsOH.

In general, the main building block for CD-MOFs is cyclodextrin (CD), a cyclic oligosaccharide that includes monosaccharide residues linked in a circular ring. Suitable cyclodextrins that can be used in the CD-MOFs include, for example, α-, β- and γ-cyclodextrins. The structure of α-1, 4-linked D-glucopyranosyl residue that can be used to form a building block in a cyclodextrin and the structure of a γ-cyclodextrin ring are shown in U.S. Pat. No. 9,085,460. Cyclodextrins can be mass-produced through enzymatic degradation of a renewable source (e.g., starch). In some embodiments, a CD-MOF can be made from one or more cyclodextrin derivatives (such as those shown in Formula (I) below).

Generally, CD-MOFs can be prepared by dissolution of both the cyclodextrin component (e.g., γ-cyclodextrin) and the metal-containing component (such as a metal salt (e.g., KCl) or a base containing a metal cation (e.g., KOH)) in a solvent (e.g., water) in which both have good solubility. Isolation of CD-MOFs can be achieved by addition of a poor solvent in which either of the above components has poor solubility. Suitable poor solvents include $C_1$-$C_{18}$ alcohols, acetone, tetrahydrofuran, dioxane, acetonitrile, and a mixture thereof.

In some embodiments, CD-MOFs can be prepared by the following method. At ambient temperatures and pressures, γ-CD can be dissolved in an aqueous solution containing an alkali metal cation (e.g., $K^+$), and followed by vapor diffusion of a water-miscible solvent (e.g., methanol) to form millimeter-sized body-centered cubic crystalline structures. Without wishing to be bound by theory, it is believed that the γ-CD rings adopt the faces of a cube, with their primary (1°) faces (C6 hydroxy (OH) groups) pointing towards the interior of the cube and their secondary (2°) faces (C2 and C3 OH groups) pointing outward. Further, without wishing to be bound by theory, it is believed that the γ-CD rings are linked together by coordination of the alkali metal cations to the primary C6 OH groups and the glycosidic ring oxygen atoms. The individual cubes pack to form the body-centered cubic crystal through coordination of more alkali metal cations to the C2 and C3 OH groups of the secondary faces of the γ-CD rings. Examples of the CD-MOF geometry are illustrated in U.S. Pat. No. 9,085,460.

In some embodiments, the CD-MOFs described herein include a CD component and a metal-containing component. The metal-containing component can have the formula MN. M can be a Group I, Group II metal or transition metal, and N can be an organic or inorganic, monovalent or multivalent anion. Suitable inorganic anions include, for example, chloride, fluoride, hydroxide, sulfide, sulfinate, carbonate, chromate, and cyanide. Suitable organic anions include, for example, benzoate, azobenzene-4,4'-dicarboxylate, acetate, and oxalate. The CD component of the CD-MOFs can be a compound of the Formula (I):

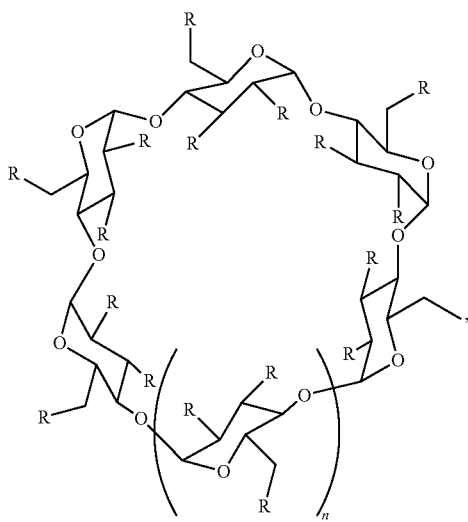

(I)

in which n=0-10; R is selected from the group consisting of —OH; —NR'R''; $C_1$-$C_{18}$ alkyl optionally substituted with one, two, three, four or five $R_1$ groups; $C_2$-$C_{18}$ alkenyl optionally substituted with one, two, three, four or five $R_1$ groups; $C_2$-$C_{18}$ alkynyl optionally substituted with one, two, three, four or five $R_1$ groups; $C_1$-$C_{18}$ alkoxy optionally substituted with one, two, three, four or five $R_1$ groups; —S(=O)$_2$R'; —S(=O)OR'; —S(=O)R'; —C(=O)OR'; —CN; —C(=O)R'; —SR', —N=N$^+$=N$^-$—; —NO$_2$, —OSO$_2$R'; —C(=O)R'; —O(=S)SR'; —P(=O)(OR')$_2$; —OP(=O)(OR')$_2$; —P(=O)(OR')R''; —N=R'R''; —NR'P(OR'')(OR'''); —OC(=O)NR'R''; aryl optionally substituted with one, two, three, four or five $R_2$ groups; heteroaryl optionally substituted with one, two, three, four or five groups independently selected from $R_2$ groups; and cycloalkyl optionally substituted with one, two, three, four or five groups independently selected from $R_2$ groups; each $R_1$ group is independently selected from the group consisting of hydroxyl, halo, $C_1$-$C_6$ alkoxy, —NR'R''; —S(=O)$_2$R'; —S(=O)OR'; —S(=O)R'; —C(=O)OR'; —CN; —C(=O)R'; —SR', —N=N$^+$=N$^-$—; —NO$_2$, —OSO$_2$R'; —C(=O)OR'; —O(=S)SR'; —P(=O)(OR')$_2$; —OP(=O)(OR')$_2$; —P(=O)(OR')R''; —N=R'R''; —NR'P(OR'')(OR'''); —OC(=O)NR'R''; aryl optionally substituted with one, two, three, four or five R' groups; heteroaryl optionally substituted with one, two, three, four or five groups independently selected from R' groups; and cycloalkyl optionally substituted with one, two, three, four or five groups independently selected from R' groups; each $R_2$ group is independently selected from the group consisting of $C_1$-$C_6$ alkyl, $C_2$-$C_6$ alkyenyl, $C_2$-$C_6$ alkynyl, hydroxyl, halo, $C_1$-$C_6$ alkoxy, —NR'R''; —S(=O)$_2$R'; —S(=O)OR'; —S(=O)R'; —C(=O)OR'; —CN; —C(=O)R'; —SR', —N=N$^+$=N$^-$—; —NO$_2$, —OSO$_2$R'; —C(=O)OR'; —O(=S)SR'; —P(=O)(OR')$_2$; —OP(=O)(OR')$_2$; —P(=O)(OR')R''; —N=R'R''; —NR'P(OR'')(OR'''); —OC(=O)NR'R''; aryl optionally substituted with one, two, three, four or five R' groups; heteroaryl optionally substituted with one, two, three, four or five groups independently selected from R' groups; and cycloalkyl optionally substituted with one, two, three, four or five groups independently selected from R' groups; and wherein each R', R'', and R''' is independently selected from the group consisting of H, $C_1$-$C_6$ alkyl, and aryl. Examples of compounds of Formula (I) include α-, β- and γ-cyclodextrins.

As used herein, the term "alkyl" refers to a straight or branched chain alkyl radical. Examples include, but are not limited, to methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Each alkyl group may be optionally substituted with one, two or three substituents such as a halo, cycloalkyl, aryl, alkenyl or alkoxy group.

As used herein, the term "lower alkenyl" refers to a straight or branched hydrocarbon radical having one or two double bonds and includes, for example, ethenyl, propenyl, 1-but-3-enyl, 1-pent-3-enyl, and 1-hex-5-enyl. The alkenyl group can also be optionally mono-, di-, or trisubstituted with, for example, halo, aryl, cycloalkyl or alkoxy.

As used herein, the term "alkynyl" refers to a straight or branched hydrocarbon radical having one or two triple bonds and includes, for example, propynyl and 1-but-3-ynyl. The alkynyl group can also be optionally mono-, di-, or trisubstituted with, for example, halo, aryl, cycloalkyl or alkoxy.

As used herein, the term "alkoxy" refers to an —O-alkyl group in which the alkyl is as defined above.

As used herein, the term "halo" or "halogen" refers to a halogen radical of fluorine, chlorine, bromine, or iodine.

As used herein, the term "aryl" refers to an aromatic carbocyclic radical having a single ring (e.g. phenyl), multiple rings (e.g. biphenyl), or multiple fused rings in which at least one is aromatic (e.g. 1,2,3,4-tetrahydronaphthyl).

As used herein, the term "heteroaryl" refers to one aromatic ring or multiple fused aromatic ring systems of 5-, 6- or 7-membered rings containing at least one and up to four heteroatoms (e.g., nitrogen, oxygen or sulfur). Examples include, but are not limited to, furanyl, thienyl, pyridinyl, pyrimidinyl, benzimidazolyl and benzoxazolyl.

As used herein, the term "cycloalkyl" refers to a carbocylic radical having a single ring (e.g., cyclohexyl), multiple rings (e.g., bicyclohexyl) or multiple fused rings (e.g., decahydronaphthalenyl). In addition, the cycloalkyl group may have one or more double bonds.

Without wishing to be bound by theory, it is believed that CD-MOFs described herein can adsorb fragrance molecules and other molecules in the fragrance compositions onto its pores and thereby reduce and stabilize the release rate of the fragrance molecules. Unexpectedly, the inventors discovered that adding a CD-MOF into a fragrance composition can maintain the fragrance intensity for a longer period of time compared to a conventional fragrance composition containing the same amount of the fragrance until the fragrance intensity drops off when the fragrance is depleted. As a result, such a composition can exhibit significantly improved scent profile (e.g., by increasing the average fragrance strength, the effective duration, and/or the fragrance fill factor of the fragrance composition). In addition, it is believed that, when CD-MOFs are loaded with fragrance molecules, CD-MOFs can act as reservoirs to store the aromas and steadily release the aromas. This is different from conventional cyclodextrins, where their utility is primarily complex formation between the host cyclodextrin and guest fragrance molecule. Specifically, when cyclodextrins form complexes with fragrance molecules, the fragrance molecules are not steadily released under ambient environment, but rather trapped indefinitely within the cyclodextrin cavities and only released by external force such as water and heat.

In general, the fragrance compositions described herein can include a suitable amount of one or more of the CD-MOFs depending on the intended uses of the compositions. In some embodiments, the CD-MOFs can be at least about 5 wt % (e.g., at least about 10 wt %, at least about 15 wt %, at least about 20 wt %, at least about 25 wt %, at least about 30 wt %, at least about 40 wt %, or at least about 50 wt %) and/or at most about 99 wt % (e.g., at most about 98 wt %, at most about 95 wt %, at most about 90 wt %, at most about 85 wt %, at most about 80 wt %, at most about 75 wt %, at most about 70 wt %, at most about 65 wt %, at most about 60 wt %, at most about 55 wt %, or at most about 50 wt %) of the fragrance compositions described herein.

In some embodiments, the fragrance compositions described herein can include at least about 0.01 µL (e.g., at least about 0.05 µL, at least about 0.1 µL, at least about 0.5 µL, at least about 1 µL, or at least about 2 µL) to at most about 10 µL (e.g., at most about 5 µL, at most about 2 µL, at most about 1 µL, at most about 0.5 µL, or at most about 0.1 µL) of the fragrance per 1 mg of the CD-MOF. Without wishing to be bound by theory, it is believed that, when the compositions contain a fragrance and a CD-MOF at an appropriate ratio (such as those described above), the compositions can exhibit significantly improved scent profile (e.g., by increasing the average fragrance strength, the effective duration, and/or the fragrance fill factor of the fragrance composition). If the fragrance to CD-MOF ratio is too high, the CD-MOF may not have a significant effect on modifying the scent profile of the fragrance. If the fragrance to CD-MOF ratio is too low, the CD-MOF may significantly suppress the release of the fragrance from the composition.

In general, the CD-MOFs in the fragrance compositions described herein are in the form of particles (e.g., crystal particles) and can have any suitable particle size depending on the intended uses of the compositions. In some embodiments, the CD-MOFs can have an average particle size of at least about 10 nm (e.g., at least about 20 nm, at least about 50 nm, at least about 100 nm, at least about 200 nm, at least about 500 nm, or at least about 1 µm) to at most about 1 cm (e.g., at most about 5 mm, a most about 1 mm, at most about 500 µm, at most about 100 µm, at most about 50 µm, at most about 10 µm, at most about 5 µm, or at most about 1 µm). It is believed that when the CD-MOFs have an average particle size from about 10 nm to about 1 µm, the fragrance compositions containing such CD-MOFs can be a suspension (e.g., a dispersion). In addition, it is believed that when the CD-MOFs have an average particle size from about 1 µm to about 1 cm, fragrance compositions containing such CD-MOFs can be an emulsion (such as a lotion, a cream, or an ointment) or a gel.

In some embodiments, the fragrance compositions described herein can optionally contain a suitable carrier, such as one or more solvents, one or more oils, or a combination thereof. The solvents that can be used in the fragrance compositions can include organic solvents, aqueous solvents (e.g., water or an aqueous solution), or a combination thereof. Exemplary organic solvents include a mineral oil, an alcohol (e.g., ethanol, isopropanol, or propylene glycol), a ketone (e.g., acetone), an ester (e.g., ethyl acetate). Exemplary aqueous solvents include water and a mixture of water and one or more other solvents (e.g., an alcohol). Exemplary oils include fractionated coconut oil, jojoba oil, grapeseed oil, and sunflower oil. In some embodiments, the fragrance compositions can include at least about 50 wt % (e.g., at least about 55 wt %, at least about 60 wt %, at least about 65 wt %, at least about 70 wt %, at least about 75 wt %, at least about 80 wt %, at least about 85 wt %, or at least about 90 wt %) and/or at most about 99 wt % (e.g., at most about 98 wt %, at most about 95 wt %, at most about 90 wt %, at most about 85 wt %, at most about 80 wt %, or at most about 75 wt %) of the carrier. In some embodiments, the fragrance compositions do not contain any carrier.

In some embodiments, the fragrance compositions described herein can include one or more optional additives, such as fixatives, emulsifiers (such as surfactants), antioxidants, preservatives, humectants, oils, thickening agents, and silicones. Exemplary fixatives include esters (e.g., benzyl salicylate, benzyl benzoate, or diethyl phthalate), alcohols, ketones, resins (e.g., benzoin, myrrh), musks (e.g., musks obtained from animals or plants, or synthetic musks (such as nitro musk compounds, polycyclic musk compounds, and macrocyclic musk compounds)), or a combination thereof. In some embodiments, the fragrance compositions described herein can include at least about 1 wt % (e.g., at least about 5 wt %, at least about 10 wt %, at least about 15 wt %, at least about 20 wt %, at least about 25 wt %, or at least about 30 wt %) and/or at most about 50 wt % (e.g., at most about 45 wt %, at most about 40 wt %, at most about 35 wt %, at most about 30 wt %, at most about 25 wt %, or at most about 20 wt %) of the fixatives. In some embodiments, the fragrance compositions do not contain any fixative.

In some embodiments, the fragrance compositions described herein can include one or more emulsifiers, such as ionic emulsifiers or non-ionic emulsifiers. For example, the emulsifiers can include lecithin, beeswax, borax, propylene glycol stearate, sorbitan tristearate, sorbitan monostearate, emulsifying wax, cetearyl alcohol, polysorbate 20, polysorbate 60, cetearyl alcohol, palm stearic, and dicetyl phosphate. In some embodiments, the composition can include at least about 0.01 wt % (e.g., at least about 0.1 wt %, at least about 0.5 wt %, at least about 1 wt %) to at most about 5 wt % (e.g., at most about 1 wt %, at most about 0.5 wt %, or at most about 0.1 wt %) of the emulsifier. Without wishing to be bound by theory, it is believed that adding an emulsifier to the fragrance can facilitate formation of emulsions. In some embodiments, the fragrance compositions do not contain any emulsifier.

In some embodiments, the fragrance compositions described herein can include two or more fragrances with different scent profiles. For example, the fragrance compositions can include (1) a first component containing a first porous CD-MOF and a first fragrance, and (2) a second component containing a second CD-MOF and a second fragrance. The first fragrance is different from the second fragrance. The first CD-MOF can be the same as or can be different from the second CD-MOF. The first component can be prepared by mixing the first CD-MOF and the first fragrance at a first ratio. The second component can be prepared by mixing the second CD-MOF and the second fragrance at a second ratio. The first ratio can be the same as or can be different from the second ratio. For example, the first ratio can be from about 0.5 µL to about 2 µL (e.g., from about 0.5 µL to about 1.5 µL, from about 0.5 µL to about 1 µL, or from about 1 µL to about 2 µL) of the first fragrance per 1 mg of the first CD-MOF and the second ratio can be from about 0.1 µL to about 0.5 µL (e.g., from about 0.25 µL to about 0.5 µL) of the second fragrance per 1 mg of the second CD-MOF. Without wish to be bound by theory, it is believed that, as the first and second fragrances are mixed with a CD-MOF at different ratios, they have different fragrance release rates and therefore exhibit different scent profiles. In some embodiments, when the first and second components are mixed, the first and second components are not substantially blended (e.g., due to relatively high viscosities of the first and second components). When such a mixture is used (e.g., applied to skin), the mixture can release the first and second fragrances at different release rates such that a user can smell different scent at different times or smell the first and second fragrances at different time periods.

In some embodiments, the first CD-MOF described above can have a first average particle size, the second CD-MOF described above can have a second average particle size, and the first average particle size is different from the second particle size. For example, the first average particle size can be from about 10 nm to about 1 µm (e.g., from about 50 nm to about 500 nm, or from about 100 nm to about 250 nm) and the second average particle size can be from about 1 µm to about 1 cm (e.g., from about 5 µm to about 5 mm, from about 10 µm to about 1 mm, from about 50 µm to 500 µm, or from about 100 µm to 250 µm). Without wish to be bound by theory, it is believed that, as the first and second fragrances are mixed with CD-MOFs having different particle sizes, they have different fragrance release rates and therefore exhibit different scent profiles.

The fragrance compositions described herein can be prepared by methods known in the art. For example, a fragrance composition can be prepared by pre-loading a fragrance onto a CD-MOF to form a mixture (e.g., by mixing a fragrance with a CD-MOF), followed by adding any optional components (e.g., optional carriers or additives) to the above mixture. As another example, a fragrance composition can be prepared by first mixing a fragrance with any optional components, followed by adding a CD-MOF into the mixture. As a further example, a fragrance composition can be prepared by first mixing a CD-MOF with any optional components, followed by adding a fragrance into the mixture.

In general, the fragrance compositions described herein can be used in any suitable cosmetic applications (such as perfumes, colognes, body sprays, hair sprays, body lotions (e.g., hand lotions), moisturizers, aftershave, deodorant, skin care products, and makeup products) and non-cosmetic applications (e.g., detergents, fabric softeners, dryer sheets, air fresheners, carpet fresheners, aromatherapy, hand sanitizers, shower gels, shampoos, liquid soaps, bar soaps, bath salts, and therapeutic or medicinal products (such as ointments, creams, syrups (e.g., cough suppression syrups), and transdermal patches (e.g., those used to ease muscle aches, joint pain, or headaches)).

The following examples are illustrative and not intended to be limiting.

Example 1: Scent Profiles of Fragrance Compositions Containing Lemon Oil

CD-MOF crystals were prepared following a similar procedure as described in U.S. Pat. No. 9,085,460. Specifically, CD-MOF crystals were grown through vapor diffusion of methanol into an aqueous solution of gamma-cyclodextrin and potassium hydroxide. The crystals were left to grow for a period of about 1 to 2 weeks, after which they were collected, filtered, washed with methanol, and then evacuated in a vacuum chamber at room temperature to approximately $10^{-3}$ Torr for 24 hours. The CD-MOF crystals were then used in the following experiments without further purification.

In the following experiments, the fragrance tested was lemon oil, which contained, among others, a fragrance compound limonene. Lemon oil was added into varying amounts of CD-MOF crystal powder with a pipette. Specifically, after the CD-MOF prepared above was placed in a VOA vial using a pipette, the lemon oil was placed on top of the CD-MOF powder, which readily soaked up the lemon oil into its porous framework.

To measure the scent profile of a fragrance composition, headspace gas chromatography was employed to measure the amount of volatile compounds present in the headspace above the fragrance composition. The headspace is the space surrounding the fragrance composition. The headspace was sampled through time to obtain the scent profile of the lemon oil (i.e., the amount of lemon oil that was vaporized into the atmosphere versus time).

To obtain a scent profile in the following experiments, a fragrance composition was placed in a VOA vial and then sealed. The vial was loaded into the headspace gas chromatography system, where two needles punctured the vial's septum top. Purge gas was fed through one needle and pressurized the vial. After a short period of time, the outlet valve was open, and the purge gas carried the headspace vapors through the other needle into the carrier gas stream that swept the headspace gas sample into the gas chromatograph column. The components in the gas stream were analyzed with a flame ionization detector (FID) at the end of the column. This approach was used to obtain the scent profiles of all of the fragrance compositions mentioned below (including fragrance compositions containing lemon oil alone, and fragrance compositions containing lemon oil and a fixative, a CD-MOF, or both).

In FIGS. 1-15, the headspace concentration of limonene for the different fragrance compositions in the experiments was measured versus time. Between the gas chromatography measurements, the fragrance compositions were kept in their vials in a water bath at 35° C. It is believed that a certain amount of the limonene may be trapped in the CD-MOF within the duration of the measurement and therefore may not be released to the headspace.

FIG. 1 is a graph showing the scent profiles of 5 µL (101), 10 µL (102), and 20 µL (103) of a lemon oil alone without any additive (e.g., a fixative or a CD-MOF). In this particular case, the graph shows the amount of limonene evaporated from the liquid lemon oil to the headspace versus time. The y-axis is the measured fragrance intensity of limonene in the headspace shown as arbitrary units (a.u.), normalized (=100) to the headspace concentration of limonene at time t=0 for a fragrance composition of 20 µL of pure lemon oil. The x-axis is time in hours. The "average fragrance intensity" is the average amount of a fragrance compound (in this case, limonene) that is in the headspace of the fragrance composition (in this case, pure lemon oil) during the life of the fragrance. The "effective duration" of the fragrance is the time when the intensity of the fragrance drops below the average fragrance intensity. A metric to quantify the performance of the fragrance composition is the "fragrance fill factor," which is the "average fragrance intensity" multiplied by its "effective duration." Maximizing the fragrance fill factor is an objective to achieve a long, stable fragrance. Preferably, the ideal scent profile is a step function, where for a given volume of a fragrance composition, the fragrance intensity measured in the headspace above the fragrance composition is relatively constant versus time until it sharply drops off when the fragrance is depleted from the fragrance composition (i.e., the fragrance compounds have completely evaporated into the headspace above). As shown in FIG. 1, the average fragrance intensity and the effective duration of this fragrance composition generally increased as the amount of the lemon oil increased. However, the fragrance intensity generally dropped off quickly after a relatively short period of time and did not remain constant over time.

Figure 2:
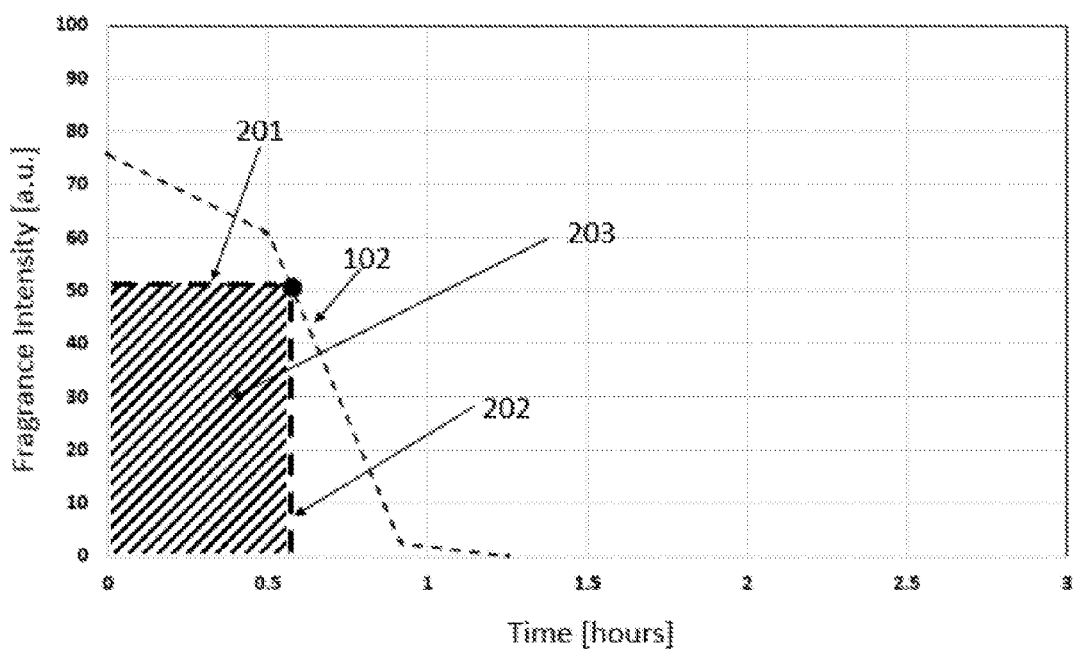
FIG. 2 is a graph showing the average fragrance intensity (201), the effective duration (202), and the fragrance fill factor (203) of 10 μL of the lemon oil (102) shown in FIG. 1.

FIG. 2 is a graph showing the average fragrance intensity (201), the effective duration (202), and the fragrance fill factor (203) of 10 μL of a lemon oil (102) shown in FIG. 1. The γ-axis is the measured fragrance intensity of limonene in the headspace shown as arbitrary units (a.u.), normalized (=100) to the headspace concentration of limonene at time t=0 for a fragrance composition of 20 μL of pure lemon oil. The x-axis is time in hours.

Figure 3:
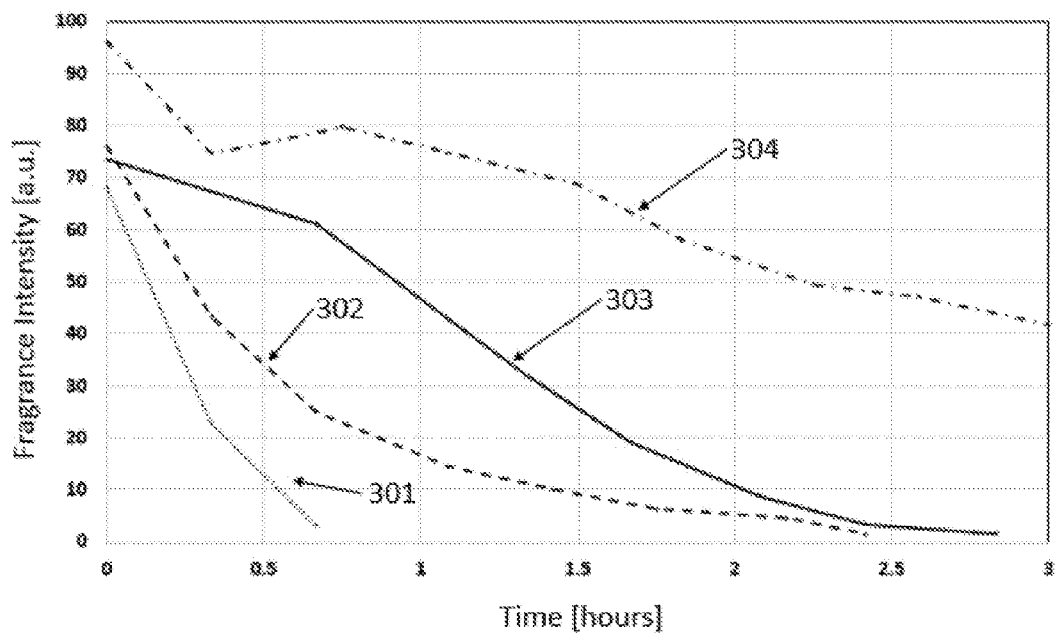
FIG. 3 is a graph showing the scent profiles of 10 μL (301), 20 μL (302), 40 μL (303) and 100 of μL (304) of mixtures containing a lemon oil and benzyl benzoate as a fixative at a volume ratio of 1:1.

FIG. 3 is a graph showing the scent profiles of 10 μL (301), 20 μL (302), 40 μL (303) and 100 μL (304) of a mixture containing a lemon oil and benzyl benzoate as a fixative at a volume ratio of 1:1. These scent profiles are representative of fragrance compounds mixed with other lower volatility aroma oils, otherwise known as the base notes of a fragrance composition. Similar to FIG. 1, the γ-axis is the measured fragrance intensity of limonene in the headspace shown as arbitrary units (a.u.), normalized (=100) to the headspace concentration of limonene at time t=0 for a fragrance composition of 20 μL of pure lemon oil. The x-axis is time in hours. As shown in FIG. 3, benzyl benzoate (i.e., a low volatile fixative) effectively slowed down the evaporation rate of limonene from pure lemon oil. However, the fixative also reduced the initial intensity of the lemon oil at t=0 (similar to diluting the amount of limonene in pure oil) and changed the scent profile to a shallower slope. In other words, the fixative is believed to "flatten" the scent profile.

Figure 4:
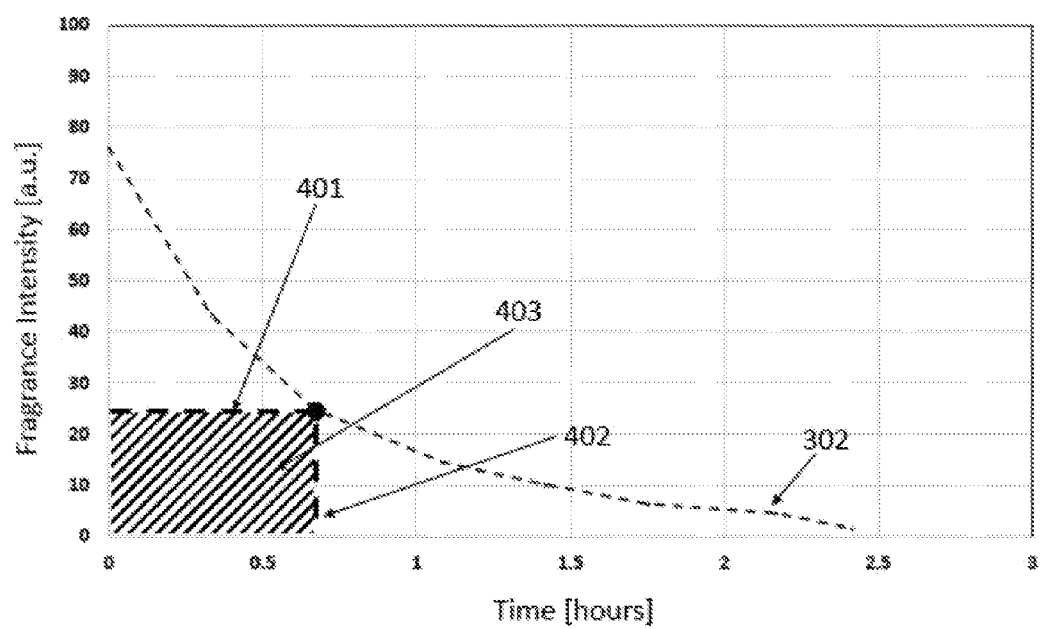
FIG. 4 is a graph showing the average fragrance intensity (401), the effective duration (402), and the fragrance fill factor (403) of 20 μL of the mixture (302) shown in FIG. 3.

FIG. 4 is a graph showing the average fragrance intensity (401), the effective duration (402), and the fragrance fill factor (403) of 20 μL of the mixture (302) shown in FIG. 3. The γ-axis is the measured fragrance intensity of limonene in the headspace shown as arbitrary units (a.u.), normalized (=100) to the headspace concentration of limonene at time t=0 for a fragrance composition of 20 μL of pure lemon oil. The x-axis is time in hours.

Figure 5:
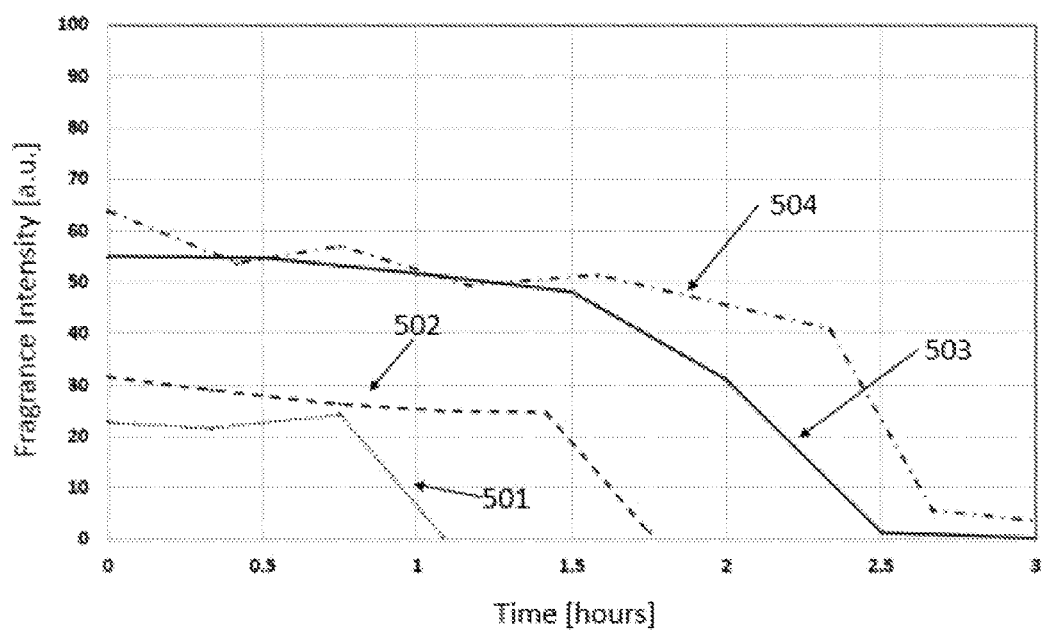
FIG. 5 is a graph showing the scent profiles of mixtures containing 5 μL (501), 10 μL (502), 20 μL (503) and 30 μL (504) of a lemon oil and a CD-MOF at a loading ratio of 1 μL of the lemon oil per 1 mg of the CD-MOF.

FIG. 5 is a graph showing the scent profiles of mixtures containing 5 μL (501), 10 μL (502), 20 μL (503) and 30 μL (504) of a lemon oil and a CD-MOF at a loading ratio of 1 μL of the lemon oil per 1 mg of the CD-MOF. The γ-axis is the measured fragrance intensity of limonene in the headspace shown as arbitrary units (a.u.), normalized (=100) to the headspace concentration of limonene at time t=0 for a fragrance composition of 20 μL of lemon oil. The x-axis is time in hours. Specifically, to obtain the graph in FIG. 5, 5 μL, 10 μL, 20 μL, and 30 μL pure lemon oil were mixed with approximately 5 mg, 10 mg, 20 mg, and 30 mg of the CD-MOF, respectively. As shown in FIG. 5, one advantage of CD-MOF over a fixative is that the CD-MOF can modify the scent profile of a fragrance composition such that the scent profile is approaching that of an ideal step function profile, where the fragrance intensity is constant and flat over time until it drops off when the fragrance compounds in the composition are depleted or stay trapped in the CD-MOF. Without wishing to be bound by theory, it is believed that, unlike a fixative, the CD-MOF does not dilute the fragrance compounds in a fragrance composition, but stores them within their pores to act as a reservoir of fragrance compounds to be released over time.

Figure 6:
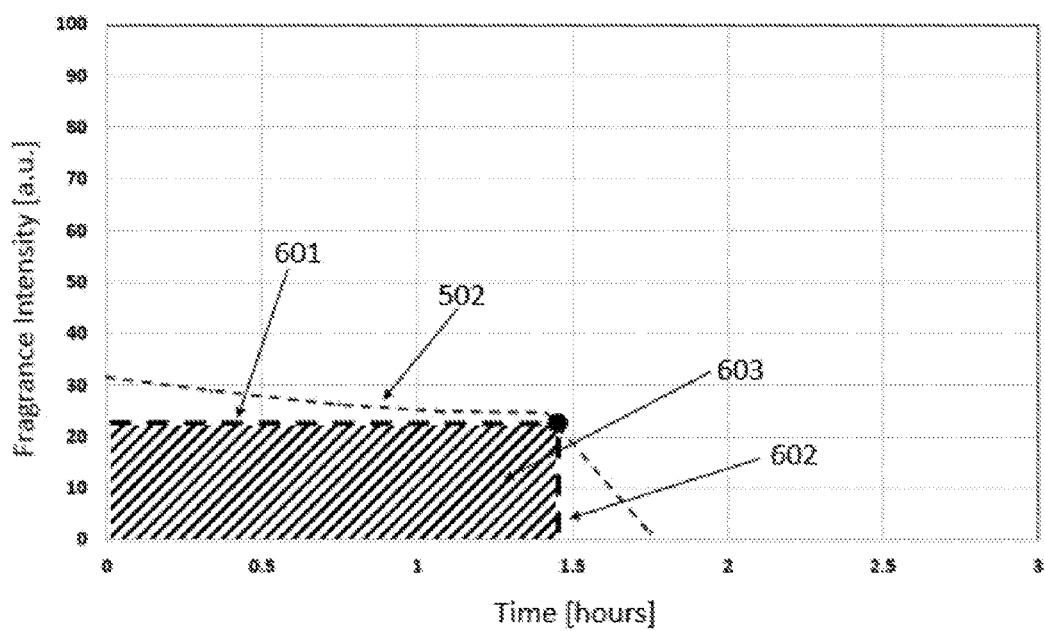
FIG. 6 is a graph showing the average fragrance intensity (601), the effective duration (602), and the fragrance fill factor (603) of the mixture (502) shown in FIG. 5.

FIG. 6 is a graph showing the average fragrance intensity (601), the effective duration (602), and the fragrance fill factor (603) of the mixture (502) shown in FIG. 5. The γ-axis is the measured fragrance intensity of limonene in the headspace shown as arbitrary units (a.u.), normalized (=100) to the headspace concentration of limonene at time t=0 for a fragrance composition of 20 μL of the lemon oil. The x-axis is time in hours. Comparing to FIGS. 2 and 3, FIG. 6 shows that the composition (502) had a longer effective duration and a larger fragrance fill factor than the composition containing the same amount of the lemon oil alone (102) and the composition containing the same amount of the lemon oil and a fixative (302).

Figure 7:
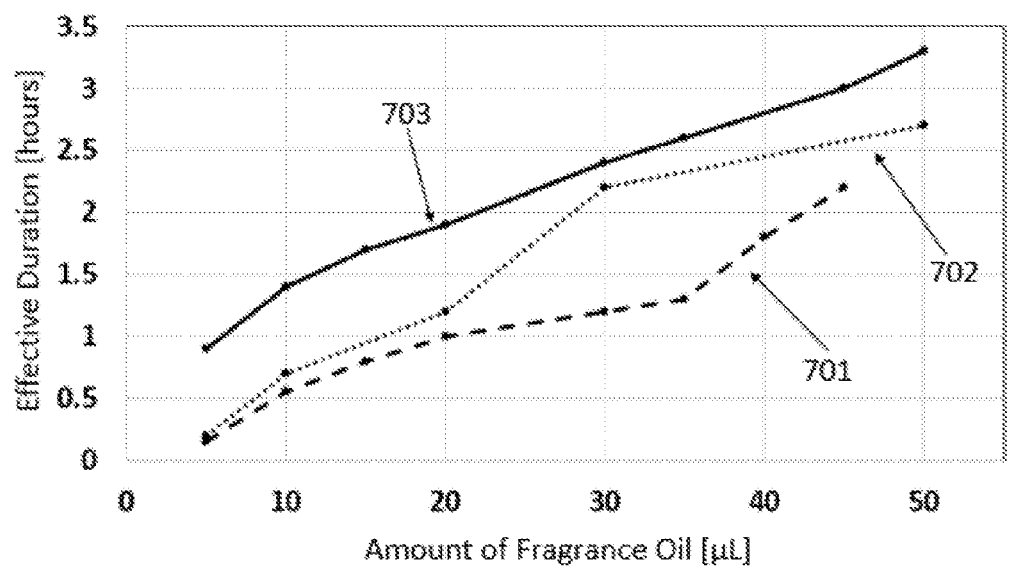
FIG. 7 is a graph showing the relationship between the effective duration and the amount of lemon oil employed for the following three fragrance compositions: a lemon oil alone (701), a mixture containing a lemon oil and benzyl benzoate as a fixative at a volume ratio of 1:1 (702), and a mixture containing a lemon oil and a CD-MOF at a loading ratio of 1 μL of the lemon oil per 1 mg of the CD-MOF (703).

FIG. 7 is a graph showing the relationship between the effective duration and the amount of lemon oil employed for the following three fragrance compositions: a lemon oil alone (701), a mixture containing a lemon oil and benzyl benzoate as a fixative at a volume ratio of 1:1 (702), and a mixture containing a lemon oil and a CD-MOF at a loading ratio of 1 μL of the lemon oil per 1 mg of the CD-MOF (703). The γ-axis is the effective duration in hours. The x-axis is the volume of the fragrance oil in the composition in μL. For composition (702), the volume of lemon oil, not the total volume of the fragrance composition, is used in the x-axis. For example, 60 μL of composition (702) contains 30 μL of lemon oil and 30 μL of benzyl benzoate, and is included in FIG. 7 at the location where x is 30 μL. As shown in FIG. 7, at the same volume of lemon oil, the fragrance composition containing the fixative (702) lasted longer than the pure lemon oil (701). Unexpectedly, the fragrance composition containing a CD-MOF (703) had a longer effective duration compared to the fragrance composition (702) that contained a conventional benzyl benzoate fixative at a 50% concentration.

Figure 8:
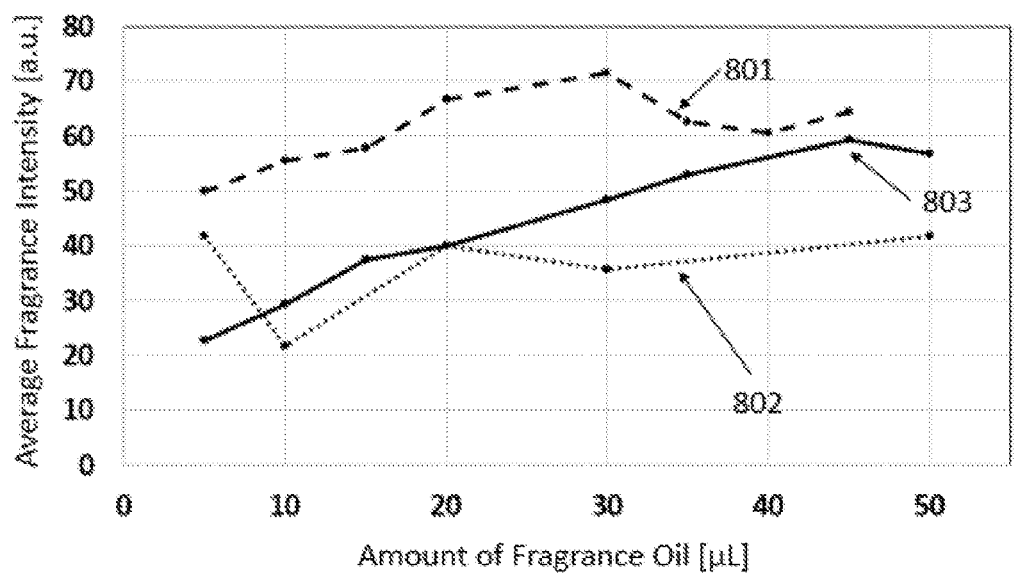
FIG. 8 is a graph showing the relationship between the average fragrance intensity and the amount of lemon oil employed for the following three fragrance compositions: a lemon oil alone (801), a mixture containing a lemon oil and benzyl benzoate as a fixative at a volume ratio of 1:1 (802), and a mixture containing a lemon oil and a CD-MOF at a loading ratio of 1 µL of the lemon oil per 1 mg of the CD-MOF (803).

FIG. 8 is a graph showing the relationship between the average fragrance intensity and the amount of lemon oil employed for the following three fragrance compositions: a lemon oil alone (801), a mixture containing a lemon oil and benzyl benzoate as a fixative at a volume ratio of 1:1 (802), and a mixture containing a lemon oil and a CD-MOF at a loading ratio of 1 μL of the lemon oil per 1 mg of the CD-MOF (803). The γ-axis is the average fragrance intensity of limonene shown as arbitrary units (a.u.), normalized (=100) to the headspace concentration of limonene at time t=0 for a fragrance composition of 20 μL of pure lemon oil. The x-axis is the volume of lemon oil in μL. For composition (802), the volume of lemon oil, not the total volume of the fragrance composition, is used in the x-axis. FIG. 8 shows that the average intensity of composition (803) was less than that of composition (801), but generally higher than that of composition (802). In other words, the results demonstrate that there is a tradeoff between the effective duration and the average fragrance intensity for a fragrance composition containing a CD-MOF at a given concentration of the fragrance.

Figure 9:
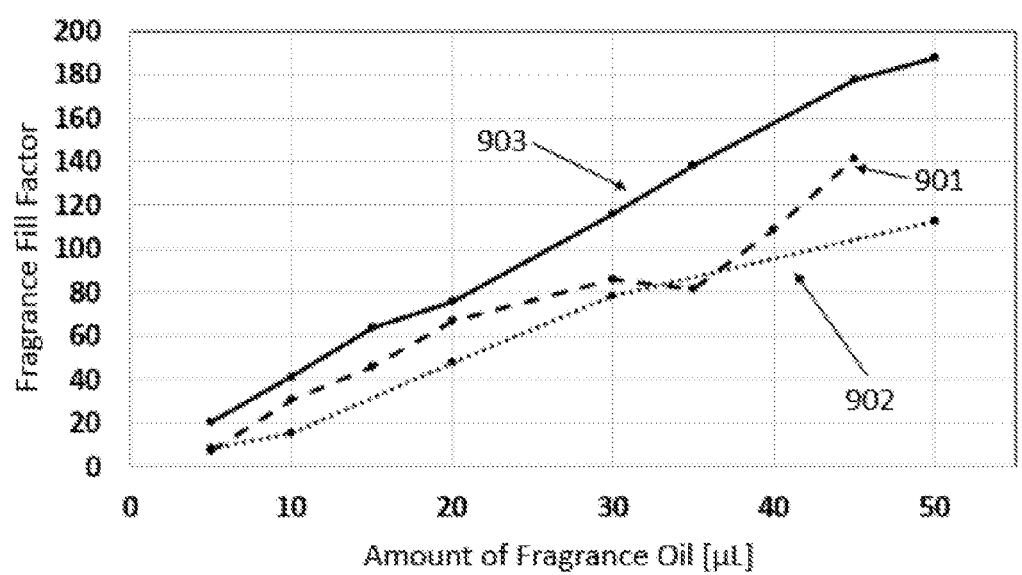
FIG. 9 is a graph showing the relationship between the fragrance fill factor and the amount of lemon oil employed for the following three fragrance compositions: a lemon oil alone (901), a mixture containing a lemon oil and benzyl benzoate as a fixative at a volume ratio of 1:1 (902), and a mixture containing a lemon oil and a CD-MOF at a loading ratio of 1 µL of the lemon oil per 1 mg of the CD-MOF (903).

FIG. 9 is a graph showing the relationship between the fragrance fill factor and the amount of lemon oil employed for the following three fragrance compositions: a lemon oil alone (901), a mixture containing a lemon oil and benzyl benzoate as a fixative at a volume ratio of 1:1 (902), and a mixture containing a lemon oil and a CD-MOF at a loading ratio of 1 μL of the lemon oil per 1 mg of the CD-MOF (903). The γ-axis is the fragrance fill factor, which is defined as the effective duration of the scent profile multiplied by the average fragrance intensity of the same scent profile. The x-axis is the volume of lemon oil in μL. As shown in FIG. 9, the composition containing a fixative (902) exhibited a slight degradation in fragrance fill factor compared to pure lemon oil (901). It is believed that, in composition (902), the degradation in average fragrance intensity exceeded the gain in effective duration, which resulted in a decrease in the overall fragrance fill factor when compared to the pure lemon oil (901). It is also believed that this decrease in fragrance fill factor is due to the fact that fixative "flattens" the scent profile too much. Unexpectedly, the fragrance composition containing the CD-MOF (903) exhibited an improvement in the fragrance fill factor compared to both pure lemon oil (901) and the composition containing a fixative (902).

Figure 10:
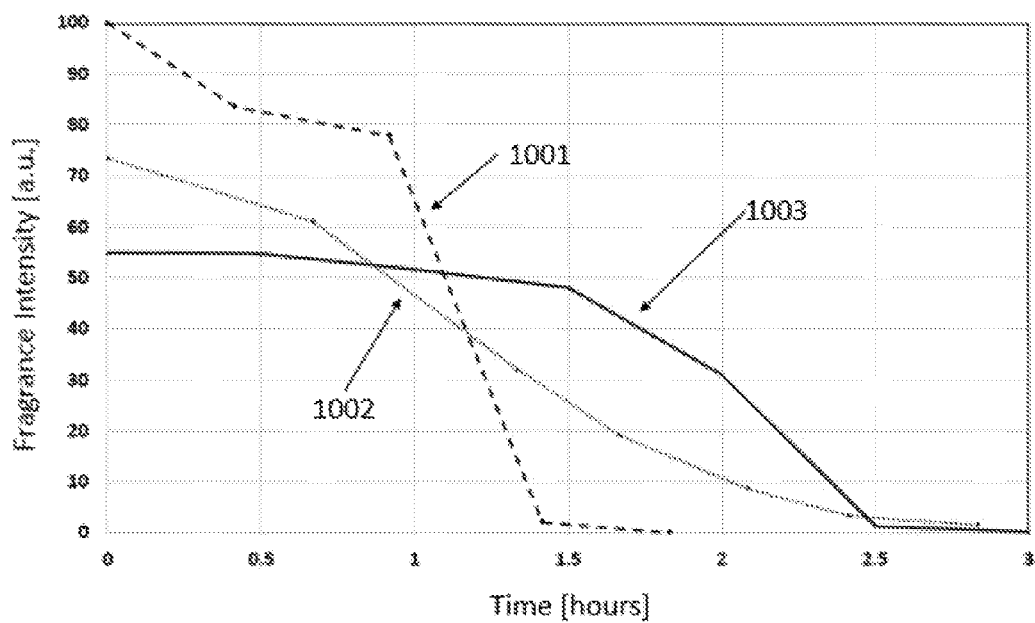
FIG. 10 is a graph comparing the scent profiles of the following three fragrance compositions that contain the same amount (i.e., 20 µL) of lemon oil: 20 µL lemon oil alone (1001), a mixture containing 20 µL lemon oil and 20 µL benzyl benzoate as a fixative (1002), and a mixture containing 20 µL lemon oil and 20 mg of a CD-MOF (1003).

FIG. 10 is a graph comparing the scent profiles of the following three fragrance compositions that contained the same amount (i.e., 20 μL) of lemon oil: 20 μL of a lemon oil alone (1001), a mixture containing 20 μL lemon oil and 20 μL benzyl benzoate as a fixative (1002), and a mixture containing 20 μL lemon oil and 20 mg of a CD-MOF (1003). The γ-axis is the measured fragrance intensity of limonene in the headspace shown as arbitrary units (a.u.), normalized (=100) to the headspace concentration of limonene at time t=0 for a fragrance composition of 20 μL of a lemon oil. The x-axis is time in hours. As shown in FIG. 10, the fixative in composition (1002) increased the duration of the fragrance composition but "flattened" it by lowering the average intensity. However, the CD-MOF unexpectedly "sharpened" the scent profile of composition (1003) by preventing excess initial evaporation of the fragrance observed in the pure lemon oil. It is believed that at least a portion of the lemon oil is held within the CD-MOF pores to be evaporated at a later time. It is also believed that the CD-MOF improves the fragrance fill factor and causes a steady release of the fragrance that is near ideal. FIG. 10 shows that the intensity of the fragrance in the headspace was substantially constant and quickly dropped off as soon as the fragrance compounds (such as limonene) were depleted from the CD-MOF pores.

As shown in FIG. 1, the lemon oil had a high initial fragrance intensity that quickly dropped off. It is believed that, since CD-MOF lowers the initial fragrance intensity, it saves and stores the fragrance compounds (which would have otherwise been lost in the high initial evaporation in the pure lemon oil) to be released later to produce a scent profile having a longer effective duration and a more constant fragrance intensity.

In conventional fragrance compositions without a fixative, the initial fragrance intensity is highest and is also the intensity first perceived by a user. A disadvantage of such a composition is that adding more fragrance does not significantly increase the duration since the additional fragrance effectively increases the intensity but not the duration. However, the CD-MOF can be added to a fragrance composition to store fragrance within its pores to act as a reservoir of the fragrance. It is believed that the CD-MOF would increase the duration and keep the intensity relatively constant over time.

Figure 11:
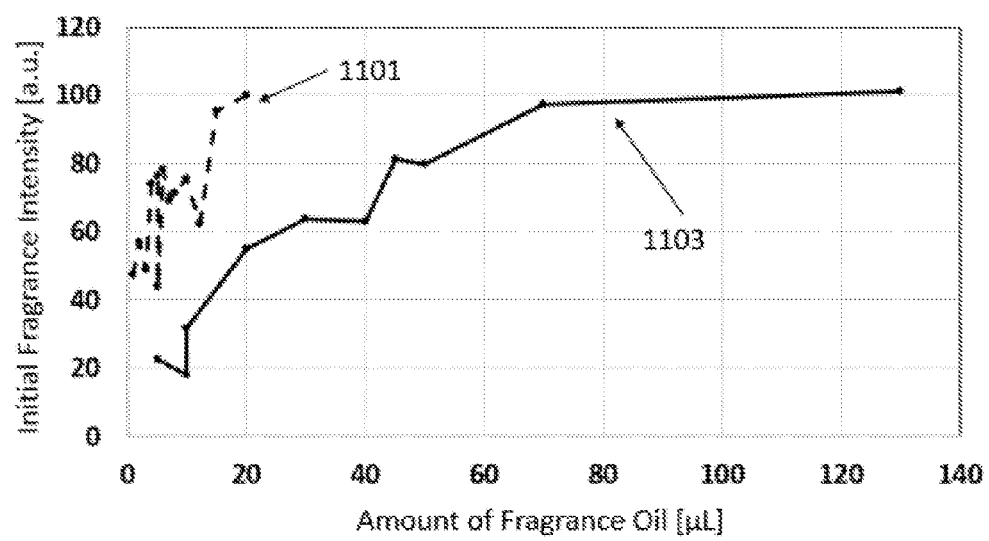
FIG. 11 is a graph showing the relationship between the initial fragrance intensity and the amount of lemon oil for the following two compositions: a lemon oil alone (1101) and a mixture containing a lemon oil and a CD-MOF at a loading ratio of 1 µL of the lemon oil per 1 mg of the CD-MOF (1103).

FIG. 11 is a graph showing the relationship between the initial fragrance intensity and the amount of lemon oil for the following two compositions: a lemon oil alone (1101) and a mixture containing a lemon oil and a CD-MOF at a loading ratio of 1 μL of the lemon oil per 1 mg of the CD-MOF (1103). The γ-axis is the initial fragrance intensity of limonene shown as arbitrary units (a.u.), normalized (=100) to the headspace concentration of limonene at time t=0 for a fragrance composition of 20 μL of a lemon oil. The x-axis is the volume of lemon oil in μL. FIG. 11 illustrates that more lemon oil can be embedded within the CD-MOF without overpowering the initial intensity of the fragrance. Employing more oil in the CDMOF will increase the overall duration of the scent profile. For example, as shown in FIG. 11, 20 μL of a lemon oil (1101) exhibited an initial fragrance intensity of 100 a.u., while a composition (1103) containing at least about 70 μL of lemon oil exhibited the same 100 a.u. initial fragrance intensity. Since the above CD-MOF fragrance composition (1103) has at least 3 times as much lemon oil as the composition (1101) containing 20 μL of a lemon oil, it is believed that the former composition would last longer than the latter composition.

Figure 12:
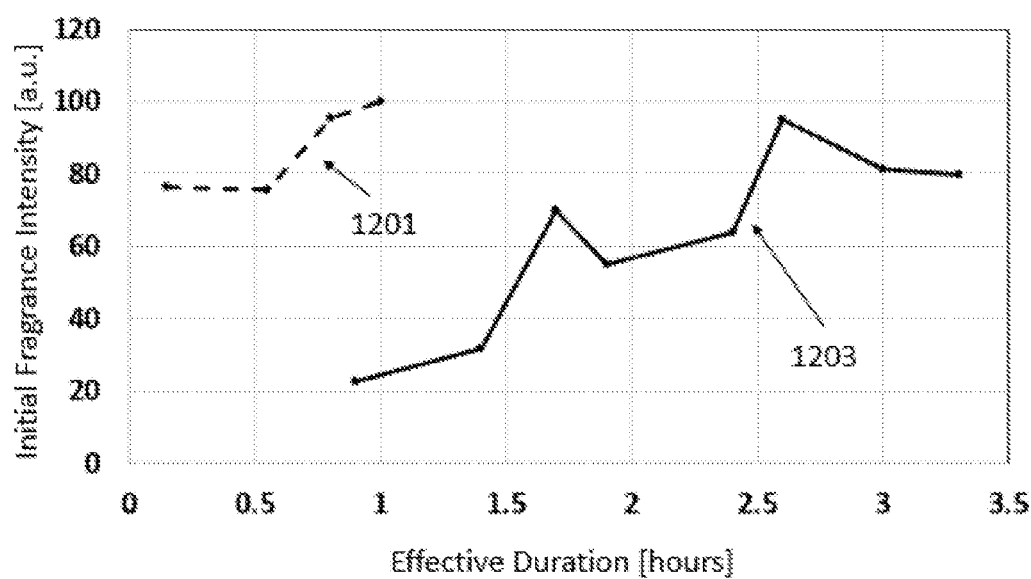
FIG. 12 is a graph showing the relationship between the initial fragrance intensity and the effective duration for the following two compositions: a lemon oil alone (1201) and a mixture containing a lemon oil and a CD-MOF at a loading ratio of 1 µL of the lemon oil per 1 mg of the CD-MOF (1203).

FIG. 12 is a graph showing the relationship between the initial fragrance intensity and the effective duration for the following two compositions: a lemon oil alone (1201) and a mixture containing a lemon oil and a CD-MOF at a loading ratio of 1 μL of the lemon oil per 1 mg of the CD-MOF (1203). The γ-axis is the initial fragrance intensity of limonene shown as arbitrary units (a.u.), normalized (=100) to the headspace concentration of limonene at time t=0 for a fragrance composition of 20 μL of a lemon oil. The x-axis is time in hours. As shown in FIG. 12, at the same initial fragrance intensity (the scent first perceived by a user when the fragrance is applied), the effective duration of the fragrance composition containing the CD-MOF (1203) was about 3 to 5 times longer than the pure lemon oil (1201).

Figure 13:
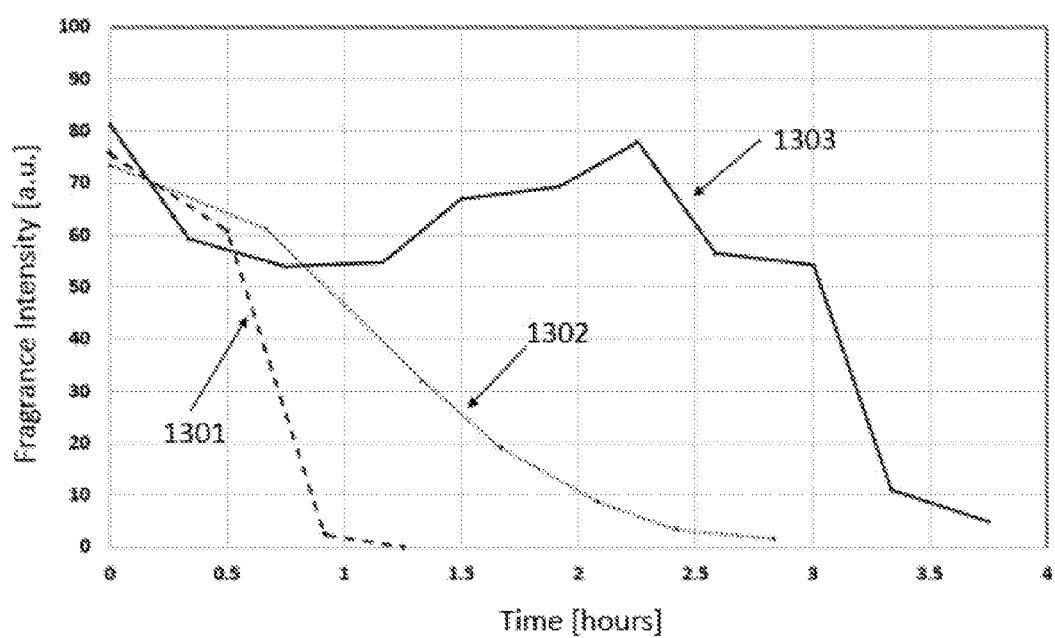
FIG. 13 is a graph showing the scent profiles of the following three compositions: 10 µL of a lemon oil alone (1301), 40 µL of a mixture containing a lemon oil and benzyl benzoate as a fixative at a volume ratio of 1:1 (1302), and a mixture containing 45 µL of a lemon oil and a CD-MOF at a loading ratio of 1 µL of the lemon oil per 1 mg of the CD-MOF (1303).

FIG. 13 is a graph showing the scent profiles of the following three compositions: 10 μL of a lemon oil alone (1301), 40 μL of a mixture containing a lemon oil and benzyl benzoate as a fixative at a volume ratio of 1:1 (1302), and a mixture containing 45 μL of a lemon oil and a CD-MOF at a loading ratio of 1 μL of the lemon oil per 1 mg of the CD-MOF (1303). The γ-axis is the measured fragrance intensity of limonene in the headspace shown as arbitrary units (a.u.), normalized (=100) to the headspace concentration of limonene at time t=0 for a fragrance composition of 20 μL of pure lemon oil. The x-axis is time in hours. As shown in FIG. 13, the three fragrance compositions had approximately the same fragrance intensity around time t=0, but the fragrance composition containing a CD-MOF (1303) had a more stable and steady fragrance intensity that was similar to the initial fragrance intensity, and this intensity lasted longer.

Figure 14:
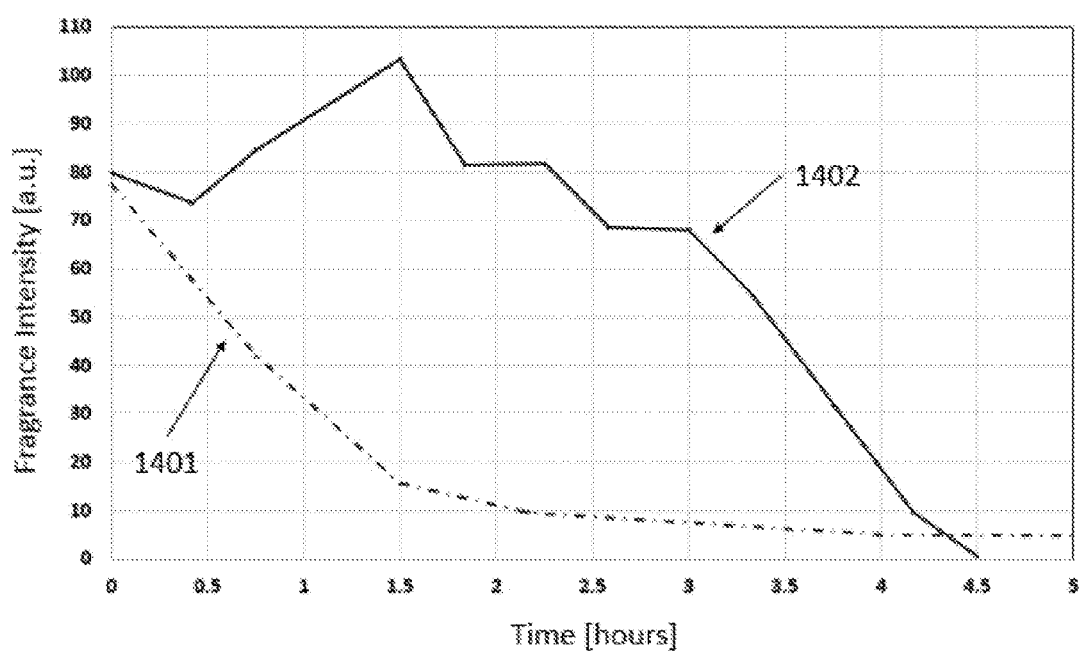
FIG. 14 is a graph showing the scent profiles of the following two compositions: a mixture containing 50 µL of a lemon oil and a CD-MOF at a loading ratio of 1 µL of the lemon oil per 4 mg of the CD-MOF (1401) and a mixture containing 50 µL of a lemon oil and a CD-MOF at a loading ratio of 1 µL of the lemon oil per 1 mg of the CD-MOF (1402).

FIG. 14 is a graph showing the scent profiles of the following two compositions: a mixture containing 50 μL of a lemon oil alone and a CD-MOF at a loading ratio of 1 μL of the lemon oil per 4 mg of the CD-MOF (1401) and a mixture containing 50 μL of a lemon oil and a CD-MOF at a loading ratio of 1 μL of the lemon oil per 1 mg of the CD-MOF (1402). The γ-axis is the measured fragrance intensity of limonene in the headspace shown as arbitrary units (a.u.), normalized (=100) to the headspace concentration of limonene at time t=0 for a fragrance composition of 20 μL of pure lemon oil. The x-axis is time in hours. As shown in FIG. 14, the fragrance composition with a lower loading ratio (1401) had a much slower fragrance release rate.

Figure 15:
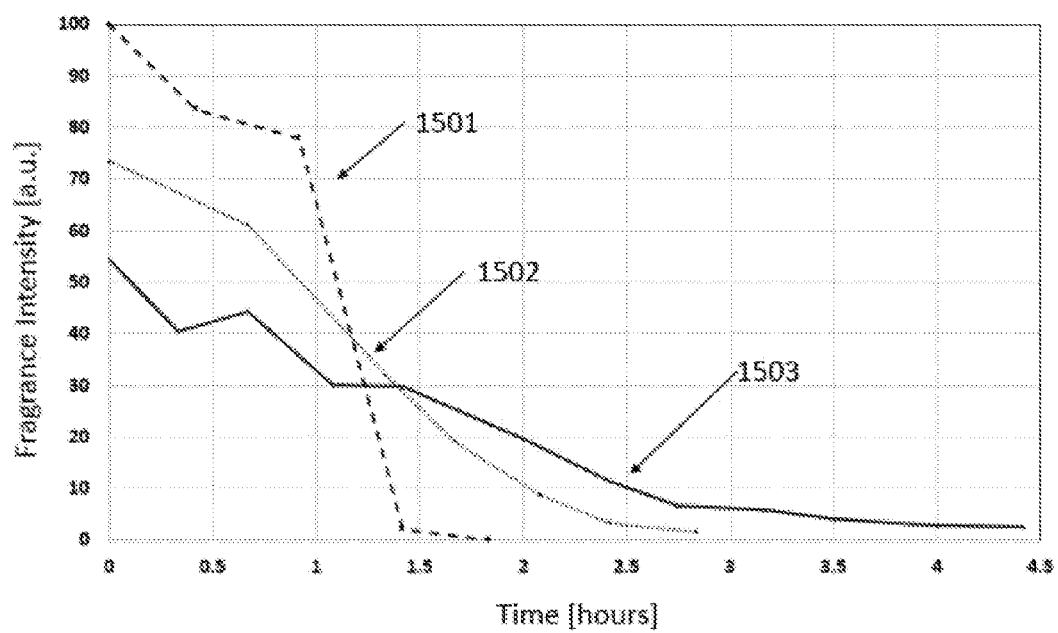
FIG. 15 is a graph showing the scent profiles of the following three compositions: 20 µL lemon oil alone (1501), 40 µL of a mixture containing a lemon oil and benzyl benzoate as a fixative at a volume ratio of 1:1 (1502), and a mixture prepared by adding 40 mg a CD-MOF into 40 µL of the mixture containing a lemon oil and benzyl benzoate as a fixative at a volume ratio of 1:1 (1503).

FIG. 15 is a graph showing the scent profiles of the following three compositions: 20 μL of a lemon oil alone (1501), 40 μL of a mixture containing a lemon oil and benzyl benzoate as a fixative at a volume ratio of 1:1 (1502), and a mixture prepared by adding 40 mg a CD-MOF into 40 μL of the mixture containing a lemon oil and benzyl benzoate as a fixative at a volume ratio of 1:1 (1503). The γ-axis is the measured fragrance intensity of limonene in the headspace shown as arbitrary units (a.u.), normalized (=100) to the headspace concentration of limonene at time t=0 for a fragrance composition of 20 μL of a lemon oil. The x-axis is time in hours. As shown in FIG. 15, composition (1503) containing both a CD-MOF and a fixative exhibited a slower release rate of the fragrance compounds than composition (1502) containing a fixative without any CD-MOF.

Example 2: Scent Profiles of Various Fragrance Compositions

The scent profiles of various fragrance compositions were measured using the same γCD-MOF obtained in Example 1 following the same measurement procedures described in Example 1 except that lemon oil was replaced with lavender essential oil, peppermint essential oil, tea tree essential oil, rosemary essential oil, wintergreen essential oil, orange essential oil, camphor essential oil, methyl salicylate, cinnamaldehyde, benzaldehyde, ethyl propionate, or allyl hexanoate.

The test results are shown in FIGS. 16-27. In FIGS. 16-27, the headspace concentration of the aromatic component was measured versus time. Thus, in these figures, the x-axis is time in hours and the γ-axis is the normalized measured fragrance intensity of the aromatic component in the headspace shown as arbitrary units (a.u.). Between the gas chromatography measurements, the fragrance compositions were kept in their vials in a water bath at 35° C. It is believed that a certain amount of the aromatic component may be trapped in the CD-MOF within the duration of the measurement and therefore may not be released to the headspace.

Figure 16:
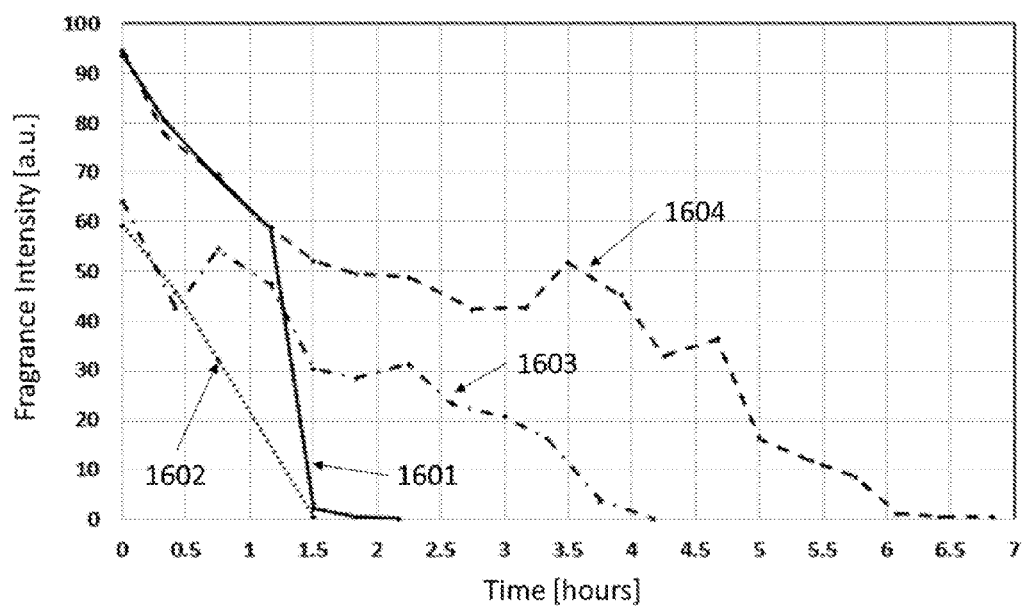
FIG. 16 is a graph showing the scent profiles of the following four compositions: 2 µL of a lavender essential oil alone (1601), and mixtures containing 1 µL (1602), 3 µL (1603), and 5 µL (1604) of a lavender essential oil and a CD-MOF at a loading ratio of 1 µL of the lavender essential oil per 1 mg of the CD-MOF.

FIG. 16 is a graph showing the scent profiles of the following four compositions: 2 μL of a lavender essential oil alone (1601), and mixtures containing 1 μL (1602), 3 μL (1603), and 5 μL (1604) of a lavender essential oil and a CD-MOF at a loading ratio of 1 μL of the lavender essential oil per 1 mg of the CD-MOF. As shown in FIG. 16, compositions (1602)-(1604) (which contained a CD-MOF) exhibited a slower release rate of the fragrance components than composition (1601) (which contained no CD-MOF). In addition, compositions (1603)-(1604) exhibited a longer release duration (in terms of both effective duration and absolute duration) of the fragrance components than composition (1601).

Figure 17:
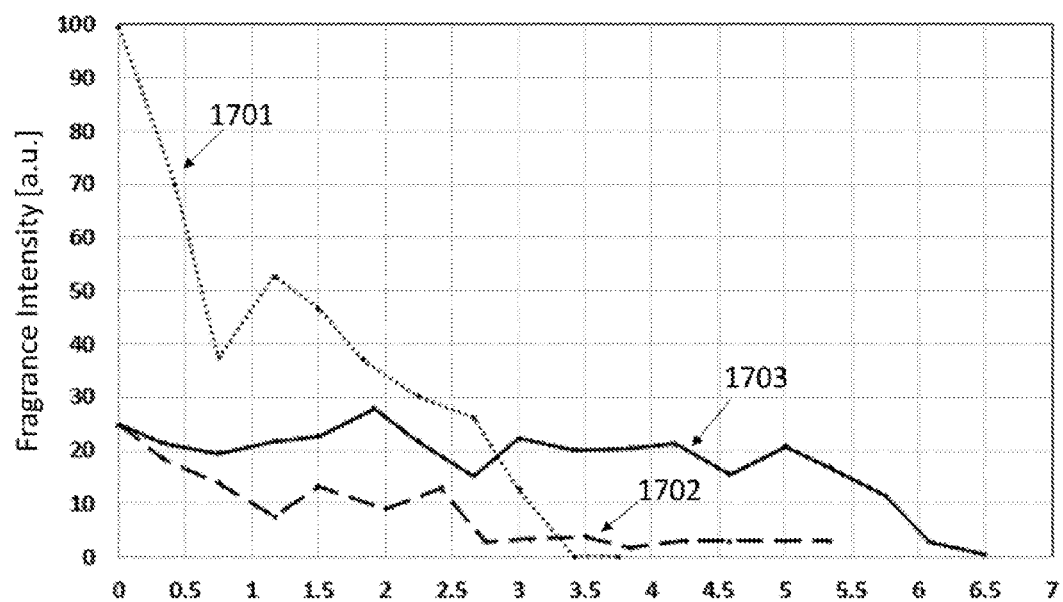
FIG. 17 is a graph showing the scent profiles of the following three compositions: 3 µL of a peppermint essential oil alone (1701), and mixtures containing 1 µL (1702) and 2 µL (1703) of a peppermint essential oil and a CD-MOF at a loading ratio of 1 µL of the peppermint essential oil per 1 mg of the CD-MOF.

FIG. 17 is a graph showing the scent profiles of the following three compositions: 3 μL of a peppermint essential oil alone (1701), and mixtures containing 1 μL (1702) and 2 μL (1703) of a peppermint essential oil and a CD-MOF at a loading ratio of 1 μL of the peppermint essential oil per 1 mg of the CD-MOF. As shown in FIG. 17, compositions (1702)-(1703) (which contained a CD-MOF) exhibited a longer release duration (in terms of both effective duration and absolute duration) and a slower and more steady release rate of the fragrance components than composition (1701) (which contained no CD-MOF) even though the former compositions contained less peppermint essential oil than the latter composition.

Figure 18:
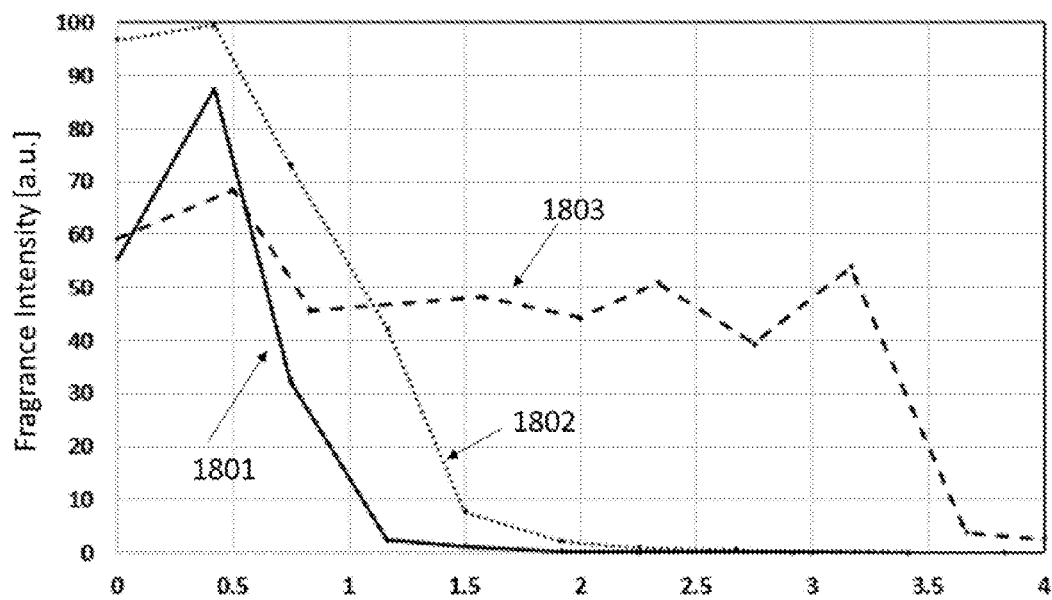
FIG. 18 is a graph showing the scent profiles of the following three compositions: 2 µL of a tea tree essential oil alone (1801), 3 µL of a tea tree essential oil (1802), and a mixture containing 5 µL of a tea tree essential oil and a CD-MOF at a loading ratio of 1 µL of the tea tree essential oil per 1 mg of the CD-MOF (1803).

FIG. 18 is a graph showing the scent profiles of the following three compositions: 2 μL of a tea tree essential oil alone (1801), 3 μL of a tea tree essential oil (1802), and a mixture containing 5 μL of a tea tree essential oil and a CD-MOF at a loading ratio of 1 μL of the tea tree essential oil per 1 mg of the CD-MOF (1803). As shown in FIG. 18, compositions (1803) (which contained a CD-MOF) exhibited a longer release duration (in terms of both effective duration and absolute duration) and a more steady release rate of the fragrance components than compositions (1801)-(1802) (which contained no CD-MOF). In addition, a comparison of compositions (1801) and (1802) shows that an increase in the amount of the tea tree essential oil substantially increased the initial fragrance intensity, but did not substantially increase the absolute release duration. By contrast, in the presence of a CD-MOF, an increase in the amount of the tea tree essential oil substantially increased the release duration, but did not increase the initial fragrance intensity. This can be advantageous as it could make the fragrance composition last longer without increasing the initial fragrance intensity (which may be considered unfavorable to certain consumers).

Figure 19:
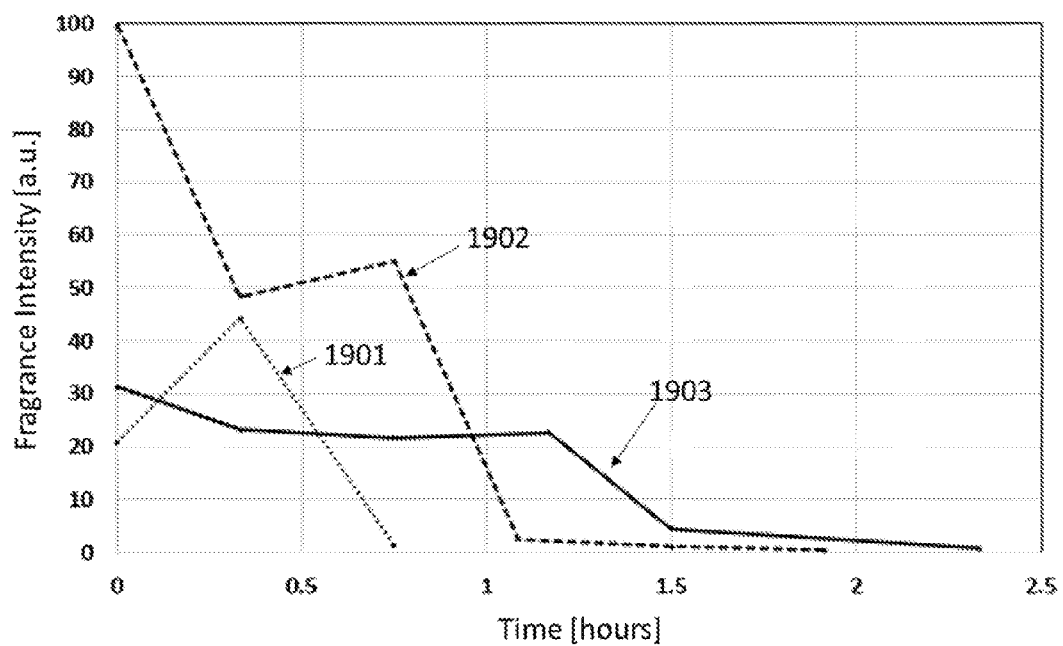
FIG. 19 is a graph showing the scent profiles of the following three compositions: 1 µL of a rosemary essential oil alone (1901), 2 µL of a rosemary essential oil (1902), and a mixture containing 4 µL of a rosemary essential oil and a CD-MOF at a loading ratio of 1 µL of the rosemary essential oil per 1 mg of the CD-MOF (1903).

FIG. 19 is a graph showing the scent profiles of the following three compositions: 1 μL of a rosemary essential oil alone (1901), 2 μL of a rosemary essential oil (1902), and a mixture containing 4 μL of a rosemary essential oil and a CD-MOF at a loading ratio of 1 μL of the rosemary essential oil per 1 mg of the CD-MOF (1903). As shown in FIG. 19, composition (1903) (which contained a CD-MOF) exhibited a longer release duration (in terms of both effective duration and absolute duration) and a more steady release rate of the fragrance components than compositions (1901)-(1902) (which contained no CD-MOF). In addition, in the presence of a CD-MOF, an increase in the amount of the rosemary essential oil in composition (1903) did not increase the fragrance intensity compared to compositions (1901)-(1902).

Figure 20:
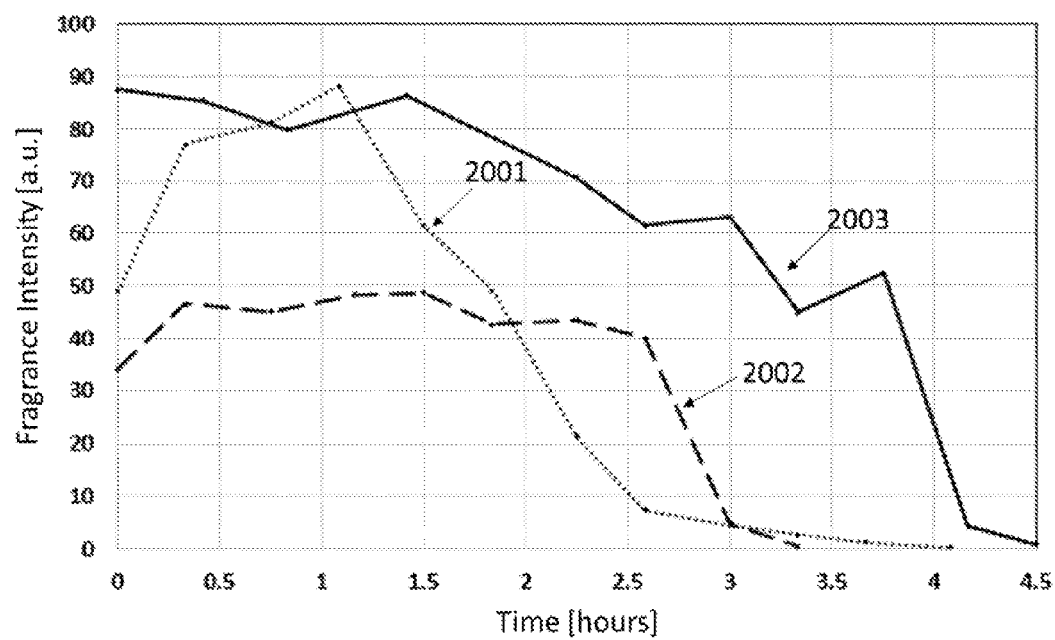
FIG. 20 is a graph showing the scent profiles of the following three compositions: 1 µL of a wintergreen essential oil alone (2001), and mixtures containing 1 µL (2002) and 2 µL (2003) of a wintergreen essential oil and a CD-MOF at a loading ratio of 1 µL of the wintergreen essential oil per 1 mg of the CD-MOF.

FIG. 20 is a graph showing the scent profiles of the following three compositions: 1 μL of a wintergreen essential oil alone (2001), and mixtures containing 1 μL (2002) and 2 μL (2003) of a wintergreen essential oil and a CD-MOF at a loading ratio of 1 μL of the wintergreen essential oil per 1 mg of the CD-MOF. As shown in FIG. 20, compositions (2002)-(2003) (which contained a CD-MOF) exhibited a longer release duration (in terms of both effective duration and absolute duration) and a more steady release rate of the fragrance components than composition (2001) (which contained no CD-MOF).

Figure 21:
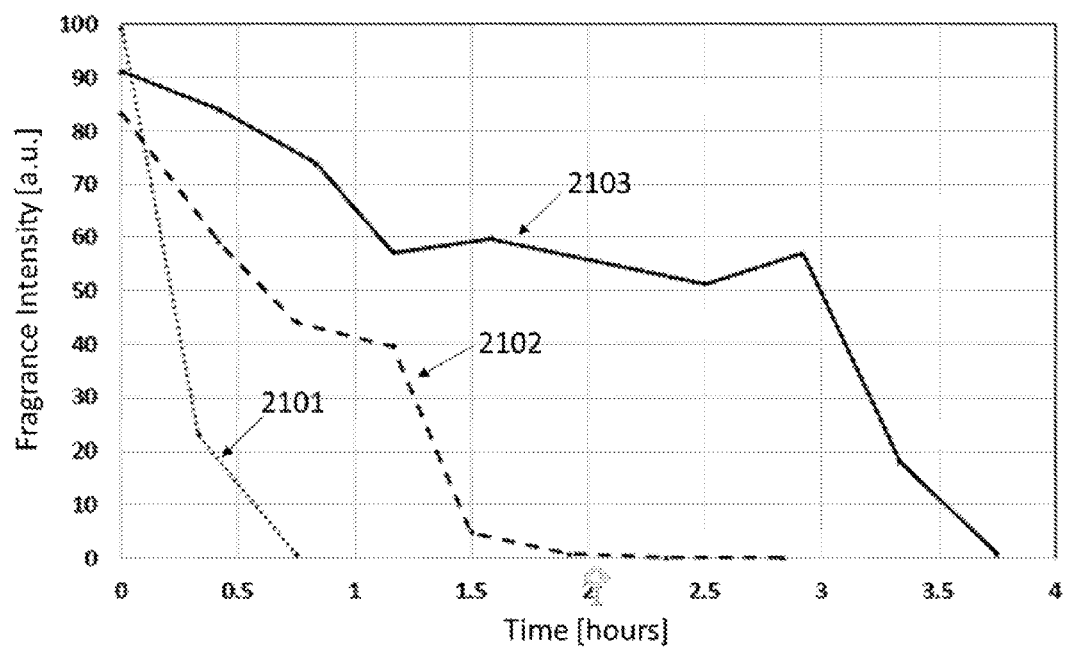
FIG. 21 is a graph showing the scent profiles of the following three compositions: 5 µL of an orange essential oil alone (2101), and mixtures containing 10 µL (2102) and 25 µL (2103) of an orange essential oil and a CD-MOF at a loading ratio of 1 µL of the orange essential oil per 1 mg of the CD-MOF.

FIG. 21 is a graph showing the scent profiles of the following three compositions: 5 μL of an orange essential oil alone (2101), and mixtures containing 10 μL (2102) and 25 μL (2103) of an orange essential oil and a CD-MOF at a loading ratio of 1 μL of the orange essential oil per 1 mg of the CD-MOF. As shown in FIG. 21, compositions (2102)-(2103) (which contained a CD-MOF) exhibited a longer release duration (in terms of both effective duration and absolute duration) and a more steady release rate of the fragrance components than composition (2101) (which contained no CD-MOF). In addition, composition (2101) had a higher initial fragrance intensity that drops off quickly compared to compositions (2102)-(2103) that has five times as much fragrance. Composition (2103) had a more constant fragrance intensity over a much longer duration.

Figure 22:
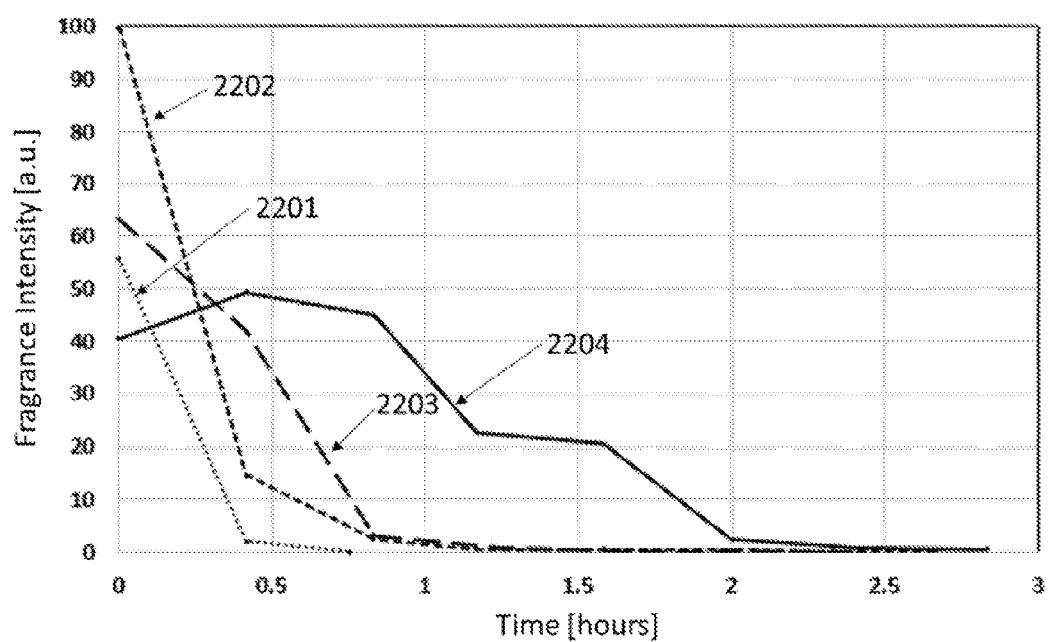
FIG. 22 is a graph showing the scent profiles of the following four compositions: 2 µL (2201) and 3 µL (2202) of a camphor essential oil alone, and mixtures containing 4 µL (2203) and 8 µL (2204) of a camphor essential oil and a CD-MOF at a loading ratio of 1 µL of the camphor essential oil per 1 mg of the CD-MOF.

FIG. 22 is a graph showing the scent profiles of the following four compositions: 2 μL (2201) and 3 μL (2202) of a camphor essential oil alone, and mixtures containing 4 μL (2203) and 8 μL (2204) of a camphor essential oil and a CD-MOF at a loading ratio of 1 μL of the camphor essential oil per 1 mg of the CD-MOF. As shown in FIG. 22, compositions (2203)-(2204) (which contained a CD-MOF) exhibited a longer release duration (in terms of both effective duration and absolute duration) and a more steady release rate of the fragrance components than compositions (2201)-(2202) (which contained no CD-MOF). In particular, a comparison of between compositions (2201) and (2202) shows that an increase in the amount of the camphor essential oil from 2 µL to 3 µL almost doubled the initial fragrance intensity, but did not substantially increase the release duration. By contrast, in the presence of a CD-MOF, an increase in the amount of the camphor essential oil substantially increased the release duration, but did not substantially increase the initial fragrance intensity.

Figure 23:
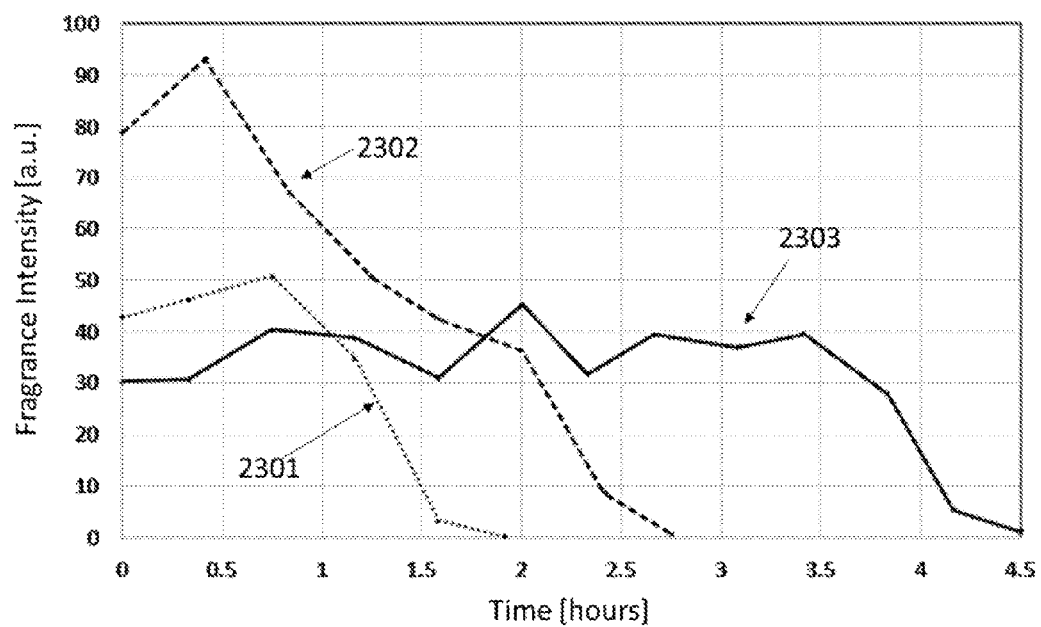
FIG. 23 is a graph showing the scent profiles of the following three compositions: 1 µL of methyl salicylate alone (2301), 2 µL of methyl salicylate (2302), and a mixture containing 2 µL of methyl salicylate and a CD-MOF at a loading ratio of 1 µL of methyl salicylate per 1 mg of the CD-MOF (2303).

FIG. 23 is a graph showing the scent profiles of the following three compositions: 1 µL of methyl salicylate alone (2301), 2 µL of methyl salicylate (2302), and a mixture containing 2 µL of methyl salicylate and a CD-MOF at a loading ratio of 1 µL of methyl salicylate per 1 mg of the CD-MOF (2303). As shown in FIG. 23, composition (2303) (which contained a CD-MOF) exhibited a longer release duration (in terms of both effective duration and absolute duration) and a slower and more steady release rate of methyl salicylate than composition (2302) (which contained no CD-MOF) even though these two compositions contained the same amount of methyl salicylate. In addition, composition (2303) exhibited a lower initial fragrance intensity than compositions (2301)-(2302).

Figure 24:
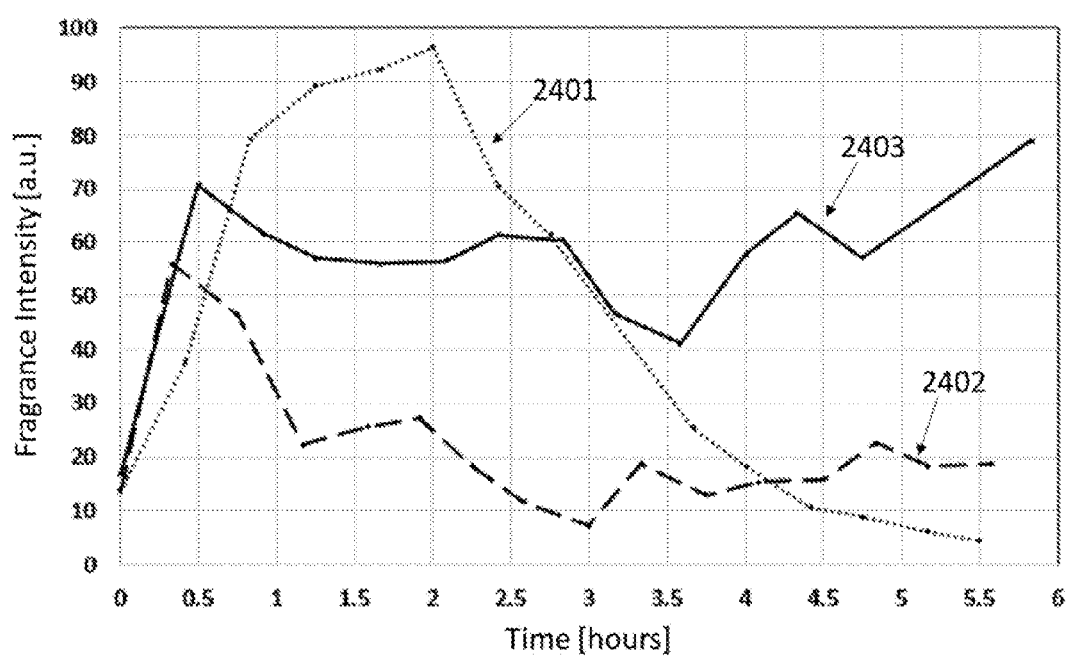
FIG. 24 is a graph showing the scent profiles of the following three compositions: 1 µL of cinnamaldehyde alone (2401), and mixture containing 1 µL (2402) and 2 µL (2403) of cinnamaldehyde and a CD-MOF at a loading ratio of 1 µL of cinnamaldehyde per 1 mg of the CD-MOF.

FIG. 24 is a graph showing the scent profiles of the following three compositions: 1 µL of cinnamaldehyde alone (2401), and mixtures containing 1 µL (2402) and 2 µL (2403) of cinnamaldehyde and a CD-MOF at a loading ratio of 1 µL of cinnamaldehyde per 1 mg of the CD-MOF. As shown in FIG. 24, composition (2402) (which contained a CD-MOF) exhibited a longer release duration (in terms of both effective duration and absolute duration) and a slower release rate of cinnamaldehyde than composition (2401) (which contained no CD-MOF) even though these two compositions contained the same amount of cinnamaldehyde. In addition, composition (2403) (which contained a CD-MOF) also exhibited a longer release duration and a slower release rate of cinnamaldehyde than composition (2401) (which contained no CD-MOF).

Figure 25:
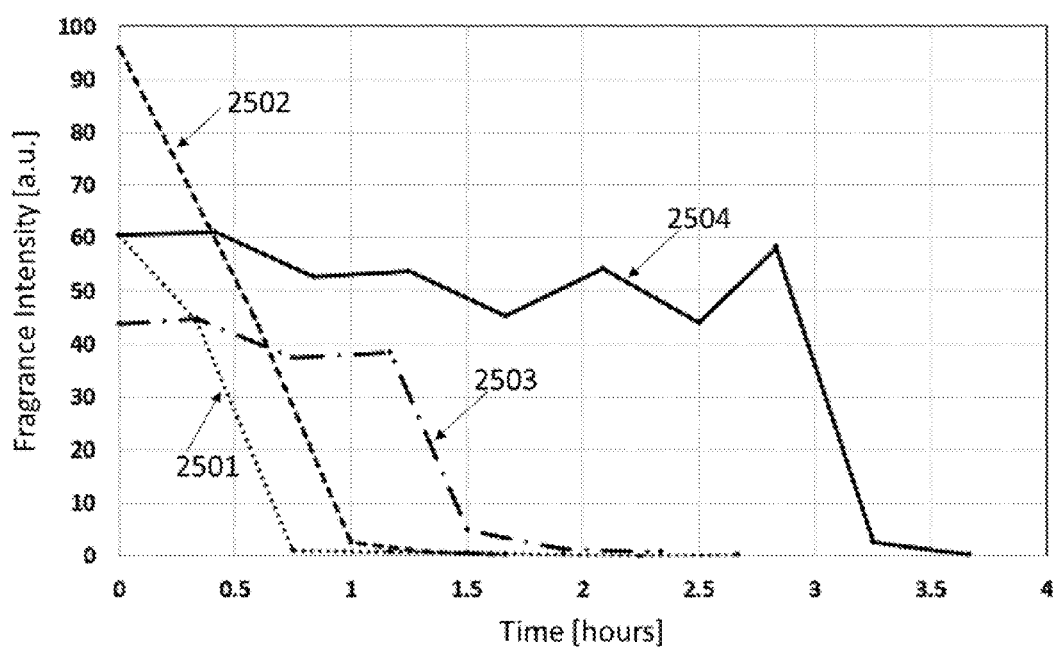
FIG. 25 is a graph showing the scent profiles of the following four compositions: 2 µL (2501) and 4 µL (2502) of benzaldehyde alone, and mixtures containing 4 µL (2503) and 12 µL (2504) of benzaldehyde and a CD-MOF at a loading ratio of 1 µL of benzaldehyde per 1 mg of the CD-MOF.

FIG. 25 is a graph showing the scent profiles of the following four compositions: 2 µL (2501) and 4 µL (2502) of benzaldehyde alone, and mixtures containing 4 µL (2503) and 12 µL (2504) of benzaldehyde and a CD-MOF at a loading ratio of 1 µL of benzaldehyde per 1 mg of the CD-MOF. As shown in FIG. 25, composition (2503) (which contained a CD-MOF) exhibited a longer release duration (in terms of both effective duration and absolute duration), and a slower and more steady release rate of benzaldehyde than composition (2502) (which contained no CD-MOF) even though these two compositions contained the same amount of benzaldehyde. In addition, composition (2503) had a substantially reduced initial fragrance intensity compared to composition (2502). Further, composition (2504) (which contained a CD-MOF) also exhibited a longer release duration and a more steady release rate of benzaldehyde than compositions (2501)-(2502) (which contained no CD-MOF).

Figure 26:
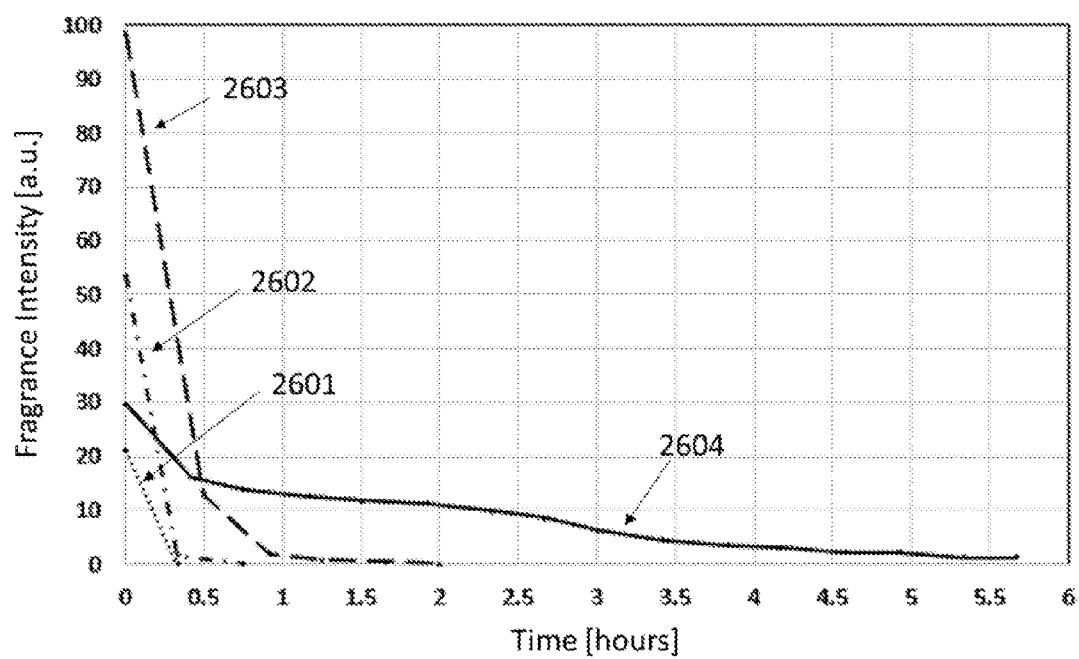
FIG. 26 is a graph showing the scent profiles of the following four compositions: 8 µL (2601), 15 µL (2602), and 30 µL (2603) of ethyl propionate alone, and a mixture containing 30 µL (2604) of ethyl propionate and a CD-MOF at a loading ratio of 1 µL of ethyl propionate per 1 mg of the CD-MOF (2604).

FIG. 26 is a graph showing the scent profiles of the following four compositions: 8 µL (2601), 15 µL (2602), and 30 µL (2603) of ethyl propionate alone, and a mixture containing 30 µL of ethyl propionate and a CD-MOF at a loading ratio of 1 µL of ethyl propionate per 1 mg of the CD-MOF (2604). As shown in FIG. 26, composition (2604) (which contained a CD-MOF) exhibited a longer release duration (in terms of both effective duration and absolute duration) and a slower release rate of ethyl propionate than composition (2603) (which contained no CD-MOF) even though these two compositions contained the same amount of ethyl propionate. In addition, a comparison of compositions (2601)-(2603) shows that increase the amount of ethyl propionate increased the initial fragrance intensity (which dropped off quickly), but had a negligible increase in the release duration.

Figure 27:
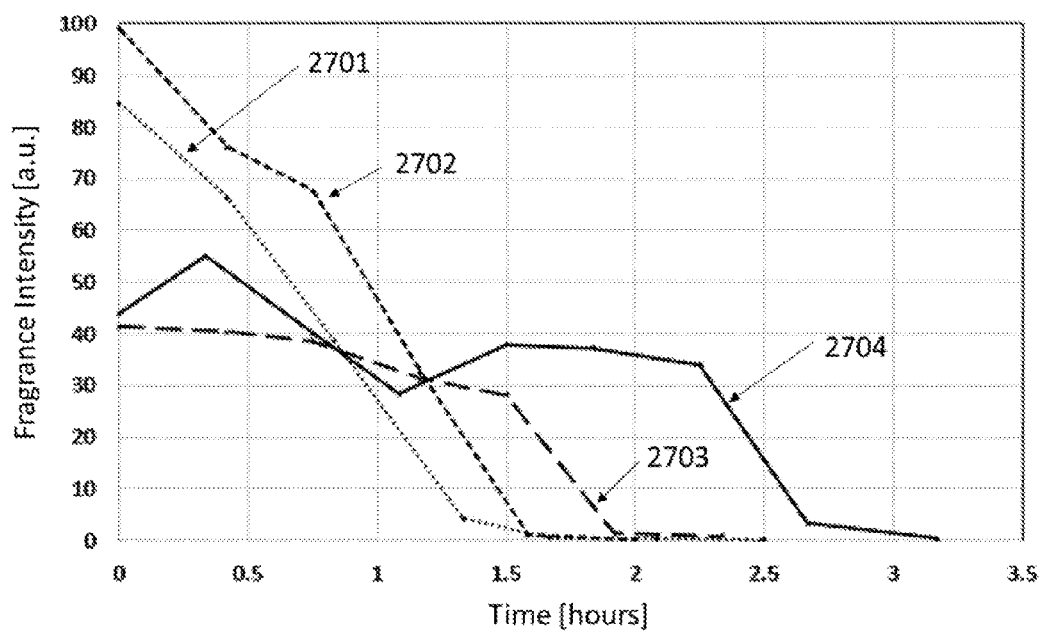
FIG. 27 is a graph showing the scent profiles of the following four compositions: 4 µL (2701) and 6 µL (2702) of allyl hexanoate alone, and mixtures containing 4 µL (2703) and 6 µL (2704) of allyl hexanoate and a CD-MOF at a loading ratio of 1 µL of allyl hexanoate per 1 mg of the CD-MOF.

FIG. 27 is a graph showing the scent profiles of the following four compositions: 4 µL (2701) and 6 µL (2702) of allyl hexanoate alone, and mixtures containing 4 µL (2703) and 6 µL (2704) of allyl hexanoate and a CD-MOF at a loading ratio of 1 µL of allyl hexanoate per 1 mg of the CD-MOF. As shown in FIG. 27, composition (2703) (which contained a CD-MOF) exhibited a longer release duration (in terms of both effective duration and absolute duration) and a slower release rate of allyl hexanoate than composition (2701) (which contained no CD-MOF) even though these two compositions contained the same amount (i.e., 4 µL) of allyl hexanoate. In addition, composition (2704) (which contained a CD-MOF) exhibited a longer release duration and a slower and more steady release rate of allyl hexanoate than composition (2702) (which contained no CD-MOF) even though these two compositions contained the same amount (i.e., 6 µL) of allyl hexanoate. Further, compositions (2703) and (2704) had a significantly reduced initial fragrance intensity compared to compositions (2701) and (2702). In particular, a comparison between compositions (2701) and (2702) shows that an increase in the amount of allyl hexanoate from 4 µL to 6 µL increased the initial fragrance intensity but did not substantially increase the effective or absolute release duration. By contrast, in the presence of a CD-MOF, an increase in the amount of allyl hexanoate from composition (2703) to composition (2704) substantially increased the effective and release duration, but did not substantially increased the initial fragrance intensity. It is believed that CD-MOF helps retain and control the release of the aroma compounds by limiting the diffusion of aroma compounds to the outer pores. It is further believed that, by loading more aroma compounds into CD-MOF, there will be a longer release duration due to a larger supply of aroma compounds stored within the CD-MOF, but the release is limited by the rate of aroma compounds diffusing to the outer surface of the CD-MOF.

Example 3: Scent Profiles of Fragrance Compositions Made from Different CD-MOFs

The scent profiles of fragrance compositions made from αCD-MOF, βCD-MOF, and γCD-MOF were obtained. γCD-MOF was prepared by using the same procedures described in Example 1. αCD-MOF and βCD-MOF were prepared by using manufacturing procedures similar to those described in Example 1 except that γCD was replaced by αCD and βCD.

Figure 28:
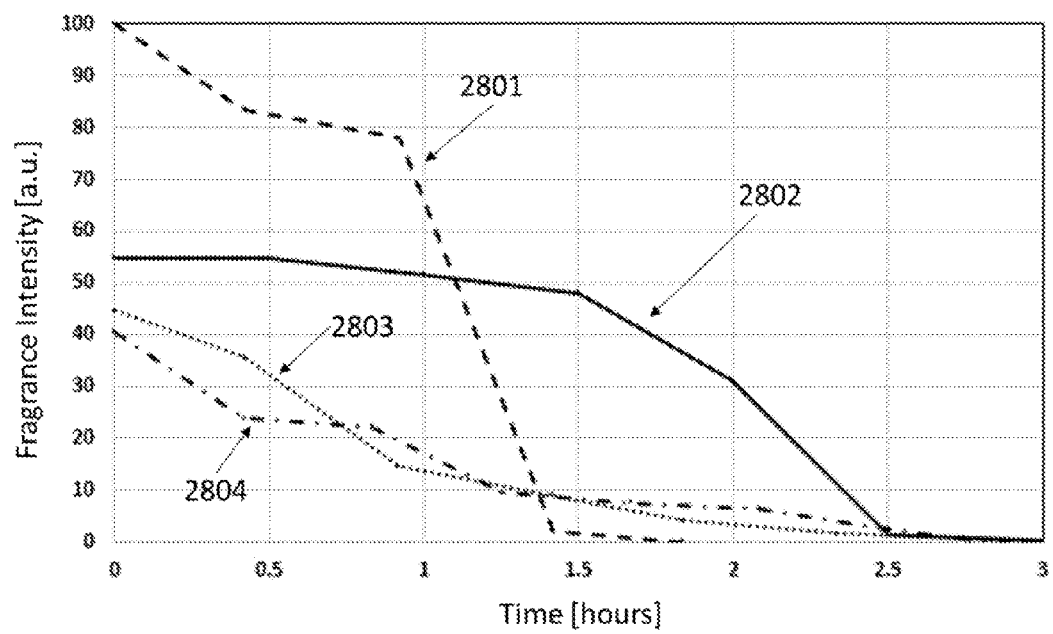
FIG. 28 is a graph showing the scent profiles of the following four compositions: 20 µL lemon oil alone (2801), a mixture containing 20 µL of lemon oil and a γCD-MOF at a loading ratio of 1 µL of lemon oil per 1 mg of the γCD-MOF (2802), a mixture containing 20 µL of lemon oil and an αCD-MOF at a loading ratio of 1 µL of lemon oil per 1 mg of the αCD-MOF (2803), and a mixture containing 20 µL of lemon oil and an βCD-MOF at a loading ratio of 1 µL of lemon oil per 1 mg of the βCD-MOF (2804).

The test results are shown in FIG. 28. In FIG. 28, the headspace concentration of the aromatic component was measured versus time. Thus, in this figure, the x-axis is time in hours and the y-axis is the normalized measured fragrance intensity of the aromatic component in the headspace shown as arbitrary units (a.u.). Between the gas chromatography measurements, the fragrance compositions were kept in their vials in a water bath at 35° C. It is believed that a certain amount of the aromatic component may be trapped in the CD-MOF within the duration of the measurement and therefore may not be released to the headspace.

FIG. 28 is a graph showing the scent profiles of the following four compositions: 20 µL lemon oil alone (2801), a mixture containing 20 µL of lemon oil and a γCD-MOF at a loading ratio of 1 µL of lemon oil per 1 mg of the γCD-MOF (2802), a mixture containing 20 µL of lemon oil and an αCD-MOF at a loading ratio of 1 µL of lemon oil per 1 mg of the αCD-MOF (2803), and a mixture containing 20 µL of lemon oil and a βCD-MOF at a loading ratio of 1 µL of lemon oil per 1 mg of the βCD-MOF (2804). As shown in FIG. 28, compositions (2802)-(2804) (which contained a CD-MOF) exhibited a longer release duration (in terms of both effective duration and absolute duration) and a slower release rate of lemon oil than composition (2801) (which contained no CD-MOF) even though these compositions contained the same amount of lemon oil.

In addition, FIG. 28 shows that compositions (2803) and (2804) (which contained αCD-MOF and βCD-MOF, respectively) released much less lemon oil than composition (2802) (which contained γCD-MOF) over the entire measurement period. Further, the area under curve calculated for composition (2802) is about the same as that calculated for composition (2801), which suggests that most of the lemon oil was released from γCD-MOF at the end of the measurement period. On the other hand, the areas under curve calculated for compositions (2803) and (2804) are smaller than that calculated for composition (2802), which suggests that a significant amount of lemon oil remained within αCD-MOF and βCD-MOF at the end of the measurement period.

Without wishing to be bound by theory, it is believed that the low release amounts from compositions (2803) and (2804) might be due to the following two factors: (1) the cavity diameters in αCD-MOF and βCD-MOF are smaller than those in γCD-MOF, and (2) αCD-MOF and βCD-MOF form long hollow needle-shaped crystals, as opposed to the hollow cube-shaped crystals formed by γCD-MOF. As a result, the lemon oil may bind to αCD-MOF and βCD-MOF more tightly than γCD-MOF, and may take a longer time to diffuse out of the long hollow needle crystals having a smaller cavity diameter than out of porous cube crystals having a larger cavity diameter.

Other embodiments are within the scope of the following claims.

What is claimed is:

1. A composition, comprising:
    a fragrance; and
    a porous cyclodextrin-based metal organic framework (CD-MOF), the CD-MOF comprising at least a metal cation and a plurality of cyclodextrin molecules;
    wherein the composition comprises a volume of the fragrance ranging from about 0.01 µL to about 10 µL per 1 mg of the CD-MOF and the fragrance has a scent profile with a step function time profile such that a time duration for a fragrance intensity of the fragrance to fall to about 50 percent of an initial fragrance intensity is greater as compared to time duration for the same volume of the fragrance alone to fall to about 50 percent of an initial fragrance intensity.

2. The composition of claim 1, wherein the composition comprises from about 0.1 µL to about 5 µL of the fragrance per 1 mg of the CD-MOF.

3. The composition of claim 1, wherein the composition comprises from about 0.5 µL to about 2 µL of the fragrance per 1 mg of the CD-MOF.

4. The composition of claim 1, wherein the CD-MOF has an average particle size of from about 10 nm to about 1 µm.

5. The composition of claim 1, wherein the CD-MOF has an average particle size of from about 1 µm to about 1 cm.

6. The composition of claim 1, further comprising a carrier that is a combination of an oil and aqueous solvent.

7. The composition of claim 1, further comprising a carrier that is an aqueous solvent and wherein the carrier is at least about 50 wt % to at most about 90 wt % of the composition.

8. The composition of claim 1, further comprising a fixative.

9. The composition of claim 8, wherein the fixative comprises an ester, an alcohol, a ketone, a resin, or a musk.

10. A composition, comprising:
    a first component comprising a first porous cyclodextrin-based metal organic framework (CD-MOF) and a first fragrance, the first CD-MOF comprising at least a first metal cation and a plurality of first cyclodextrin molecules; and
    a second component comprising a second CD-MOF and a second fragrance, the second CD-MOF comprising at least a second metal cation and a plurality of second cyclodextrin molecules;
    wherein the first component is prepared by mixing the first CD-MOF and the first fragrance at a first ratio, the second component is prepared by mixing the second CD-MOF and the second fragrance at a second ratio, and the first ratio is different from the second ratio.

11. The composition of claim 10, wherein the first fragrance is different from the second fragrance.

12. The composition of claim 10, wherein the first component comprises from about 0.5 µL to about 2 µL of the first fragrance per 1 mg of the first CD-MOF.

13. The composition of claim 10, wherein the second component comprises from about 0.1 µL to about 0.5 µL of the second fragrance per 1 mg of the second CD-MOF.

14. The composition of claim 10, wherein the first CD-MOF has a first average particle size, the second CD-MOF has a second average particle size, and the first average particle size is different from the second particle size.

15. The composition of claim 14, wherein the first average particle size is from about 10 nm to about 1 µm.

16. The composition of claim 14, wherein the second average particle size is from about 1 µm to about 1 cm.

17. A composition, comprising:
    a fragrance; and
    a porous cyclodextrin-based metal organic framework (CD-MOF), the CD-MOF having an average particle size of from about 10 nm to about 1 cm and comprising at least a metal cation and a plurality of cyclodextrin molecules;
    wherein the composition is a suspension, an emulsion, or a gel.

18. The composition of claim 17, wherein the CD-MOF has an average particle size of from about 10 nm to about 1 µm.

19. The composition of claim 17, the CD-MOF has an average particle size of from about 1 µm to about 1 cm.

20. The composition of claim 10, further comprising a carrier that is an oil or an organic solvent.

21. The composition of claim 10, further comprising a carrier that is an aqueous solvent and the composition of the fragrance and the CD-MOF is at least about 50 wt % to at most about 90 wt % of the carrier.

22. The composition of claim 17, further comprising a carrier that is an oil or an organic solvent.

23. The composition of claim 17, further comprising a carrier that is an aqueous solvent and the composition of the fragrance and the CD-MOF is at least about 50 wt % to at most about 90 wt % of the carrier.

24. The composition of claim 1, wherein the cyclodextrin molecules are gamma cyclodextrin and the metal cation is a potassium cation.

25. The composition of claim 6, wherein the aqueous solvent is water.

26. The composition of claim 7, wherein the aqueous solvent is water.

\* \* \* \* \*